US007323174B1

(12) United States Patent
Marchalonis et al.

(10) Patent No.: US 7,323,174 B1
(45) Date of Patent: Jan. 29, 2008

(54) MODULATION OF IMMUNE RESPONSE AND METHODS BASED THEREON

(75) Inventors: John J. Marchalonis, Tucson, AZ (US); Ronald R. Watson, Tucson, AZ (US); Samuel F. Schluter, Tucson, AZ (US)

(73) Assignee: Arizona Board of Regents on behalf of The University of Arizona, Tucson, AZ (US)

( * ) Notice: Subject to any disclaimer, the term of this patent is extended or adjusted under 35 U.S.C. 154(b) by 0 days.

(21) Appl. No.: 09/591,789

(22) Filed: Jun. 12, 2000

(51) Int. Cl.
*A61K 39/21* (2006.01)
(52) U.S. Cl. .................. 424/185.1; 424/208.1
(58) Field of Classification Search ............ 435/5; 530/326, 300; 424/185.1, 278.1, 188.1, 208.1; 475/7.24
See application file for complete search history.

(56) References Cited

U.S. PATENT DOCUMENTS

| 5,911,990 | A | 6/1999 | Marchalonis et al. |
| 5,962,319 | A | 10/1999 | Ogawa et al. |
| 6,150,337 | A | 11/2000 | Tam |
| 2004/0248192 | A1 | 12/2004 | Marchalonis et al. |

FOREIGN PATENT DOCUMENTS

| EP | 0 109 942 | 5/1984 |
| EP | 0 180 564 | 5/1986 |
| EP | 0 231 039 | 8/1987 |
| GB | 2 189 141 | 10/1987 |
| WO | WO 91/10736 | 7/1991 |
| WO | WO 92/01715 | 2/1992 |
| WO | WO 94/18317 | 8/1994 |
| WO | WO 95/18145 | 7/1995 |
| WO | WO 96/21028 | 7/1996 |
| WO | WO 97/35991 | 10/1997 |
| WO | WO 02/094860 | 11/2002 |

OTHER PUBLICATIONS

Davis, M. M. and Y.-H. Chien, 1999, "T-cell antigen receptors", in Fundamental Immunology, Fourth Edition, W. E. Paul, ed., Lippincott-Raven Publishers, Philadelphia, pp. 341-344, 346, and 347.*
Graziosi, C., et al., 1994, "Lack of evidence for dichotomy of $T_H1$ and $T_H2$ predominance in HIV-infected individuals", Science 265:248-252.*
Maggi, E., et al., 1994, "Ability of HIV to promote a $T_H1$ to $T_H0$ shift and to replicate preferentially in TH2 and TH0 cells", Science 265:244-248.*
Romagnani, S., et al., 1994, "An alternative view of the Th1/Th2 switch hypothesis in HIV infection", AIDS Res. Human Retrovir. 10(5):III-IX.*
Shearer, G. M. and M. Clerici, 1992, "T helper cell immune dysfunction in asympotomatic, HIV-1-seropositive individuals: the role of TH1-TH2 cross-regulation", Chem. Immunol. 54:21-43.*

Yarchoan, R. and S. Broder, 1992, "Correlations between the in vitro and in vivo activity of anto-HIV agents: implications for future drug development", J. Enzyme Inhibit. 6:99-111.*
Gait, M. J. and K. Karn, 1995, "Progress in anti-HIV structure based design", TIBTECH 13:430-438.*
Öberg, B. and. L. Vrang, 1990, "Screening for new agents", Eur. J. Clin Microbiol. Infect. Dis. 9(7):466-471.*
Evavold, B. D., et al., 1993, "Tickling the TCR: selective T-cell functions stimulated by altered peptide ligands", Immunol. Today 14(12):602-9 (abstract provided).*
Mandrenas, J. and R. N. Germain, 1996, "Variant TCR ligands: new insights into the molecular basis of antigen-dependent signal transduction and T-cell activation", Sem. Immunol. 8(2):83-101 (abstract provided).*
Liang, B., et al., 1998, Injection of T-cell receptor peptide reduces immunosenescence in aged C57BL/6 mice, Immunol. 93:462-468.*
Liang, B., et al., 1996, T-cell receptor dose and the time of treatment during murine retrovirus infection for maintenance of immune function, Immunol. 87:198-204.*
Liang, B., et al., 1996, Effects of vaccination against different T cell receptors on maintenance of immune function during murine retrovirus infection, Cell. Immunol. 172:126-134.*
Watson, R. R., et al., T cell receptor Vβ complementarity-determining region 1 peptide administration moderates immune dysfunction and cytokine dysregulation induced by murine retrovirus infection, J. Immunol. 155:2282-2291.*
Watson, R. R., et al., T cell receptor Vβ complementarity-determining region 1 peptide administration moderates immune dysfunction and cytokine dysregulation induced by murine retrovirus infection, 1995 J. Immunol. 155:2282-2291.*
Marchalonis et al., 2001, *T-Cell Receptor-Derived Peptides in Immunoregulation and Therapy of Retrovirally Induced Immunosuppression*, Critical Reviews in Immunology 21:57-74.
Sepulveda et al., 2003, *T-Cell Receptor Vβ8.1 Peptide Reduces Coxsackievirus-induced Cardiopathology during Murine Acquired Immunodeficiency Syndrome*, J. Cardiovasc. Pharmacol. 41:489-497.
Lake et al., 1994, *Autoantibodies to the α/β T-cell receptors in human immunodeficiency virus infection: Dysregulation and mimicry*, Proc. Natl. Acad. Sci. USA 91:10849-10853.
Marchalonis et al., 1994. *Synthetic Autoantigens of Immunoglobulins and T-Cell Receptors: Their Recognition in Aging, Infection, and Autoimmunity*, Proceedings of the Society for Experimental Biology and Medicine pp. 129-147, Academic Press, NY.

(Continued)

Primary Examiner—Jeffrey S. Parkin
(74) Attorney, Agent, or Firm—Jones Day

(57) ABSTRACT

The present invention relates to methods for the prevention and/or treatment of cardiovascular and allergic diseases and disorders, methods for inhibiting the growth of, or reducing the volume of, a solid tumor, as well as methods for preventing progression to AIDS in an HIV-infected human, by administering a peptide derived from T cell receptors, or a derivative thereof. The present invention also relates to peptides derived from T-cell receptors, and derivatives thereof, which are useful in such methods.

4 Claims, No Drawings

OTHER PUBLICATIONS

Marchalonis et al., 1997, *Analysis of Autoantibodies to T-Cell Receptors Among HIV-infected Individuals: Epitope Analysis and Time Course*, Clinical Immunology and Immunopathy 82(2):174-189.

Akuffo et al., 1999, "Natural killer cells in cross-regulation of IL-12 by IL-10 in Leishmania antigen-stimulated blood donor cells," Clin. Exp. Immunol. 117(3):529-34.

Albright et al., 2000, "Soluble receptors and other substances that regulate Proinflammatory cytokines in young and aging humans," J. Gerontol. A Biol. Sci. Med. Sci. 55(1):B20-5.

Aleman et al., 2000, "Interleukin-12 amplifies the M. leprae hsp65-cytotoxic response in the presence of tumour necrosis factor-alpha and interferon-gamma generating CD56+ effector cells: interleukin-4 downregulates this effect," Scand. J. Immunol. 51(3):262-70.

Boon, 1993, "Tumor antigens recognized by cytolytic T lymphocytes: present perspectives for specific immunotherapy," Int. J. Cancer 54(2):177-80.

Bourdette et al., 1994, "Immunity to TCR peptides in multiple sclerosis. I. Successful immunization of patients with synthetic V beta 5.2 and V beta 6.1 CDR2 peptides," J. Immunol. 152(5):2510-9.

Bradley et al., 1994, "Alteration of in vivo cytokine gene expression in mice infected with a molecular clone of the defective MAIDS virus," J. Acquir. Immune Defic. Syndr. 7(1):1-9.

Castle et al., 1997, "Evidence of enhanced type 2 immune response and impaired upregulation of a type 1 response in frail elderly nursing home residents,"Mech. Ageing Dev. 94(1-3):7-16.

Cherwinski et al., 1987, "Two types of mouse helper T cell clone. III. Further differences in lymphokine synthesis between Th1 and Th2 clones revealed by RNA hybridization, functionally monospecific bioassays, and monoclonal antibodies," J. Exp. Med. 166(5):1229-44.

Clerici et al., 1993, "A TH1→TH2 switch is a critical step in the etiology of HIV infection," Immunol. Today 14(3):107-11.

De Carli et al., 1994, "Human Th1 and Th2 cells: functional properties, regulation of development and role in autoimmunity," Autoimmunity 18(4):301-8.

Dehghanpisheh et al., 1995, "Production of IgG autoantibodies to TCRs in mice infected with the retrovirus LP-BM5." Int. Immunol. 7(1):31-6.

Dehghanpishah et al., 1997, "Retrovirally induced mouse anti-TCR monoclonals can synergize the in vitro proliferative T cell response to bacterial superantigens," Scan.J. Immunol. 45(6):645-54.

Fauci et al., 1993, "Multifactorial nature of human immunodeficiency virus disease: implications for therapy," Science 262(5136):1011-8.

Fernandez-Gutierrez et al., 1999, "Early lymphocyte activation in elderly humans: impaired T and T-dependent B cell responses," Exp. Gerontol. 34(2):217-29.

Garcia et al., 1999, "IL-18 promotes type 1 cytokine production from NK cells and T cells in human intracellular infection," J. Immunol. 162(10):6114-21.

Gazzinelli et al., "CD4+ subset regulation in viral infection. Preferential activation of the Th2 cells during progression of retrovirus-induced immunodeficiency in mice," J. Immunol. 148(1):182-8.

Graziosi et al., 1996, "Kinetics of cytokine expression during primary human immunodeficiency virus type 1 infection," Proc. Natl. Acad. Sci. U.S.A. 93(9):4386-91.

Haynes et al., 1996, "Toward an understanding of the correlates of protective immunity to HIV infection," Science. Jan. 19, 1996;271(5247):324-8.

Hirsch et al., 1999, "Depressed T-cell interferon-gamma responses in pulmonary tuberculosis: analysis of underlying mechanisms and modulation with therapy,"J. Infect. Dis. 180(6):2069-73.

Imberti et al., 1991, Selective depletion in HIV infection of T cells that bear specific T cell receptor V beta.

Infante-Duarte et al., 1999, "Th1/Th2 blance in infection,"Springer Semin. Immunopathol. 21(3):317-38.

Ishikawa et al., 1998, "Polyclonality and multispecificity of the CTL response to a single viral epitope," J. Immunol. 161(11):5842-50.

Jolly et al., 1999, "Calorie restriction modulates Th-1 and Th2 cytokine-induced immunoglobulin secretion in young and old C57BL/6 cultured submandibular glands," Aging (Milano) 11(6):383-9.

Kanagawa et al., 1993, "Resistance of mice deficient in IL-4 to retrovirus-induced immunodeficiency syndrome (MAIDS)," Science 262(5131):240-2.

Karanfilov et al., 1999, "Age-related defects in Th1 and Th2 cytokine production by human T cells can be dissociated from altered frequencies of CD45RA+ and CD45RO+ T cell subsets," Mech. Ageing Dev. 109(2):97-112.

Kawakami et al., 1997, "Human tumor antigens recognized by T-cells," Immunol. Res. 16(4):313-39.

Kenney et al., 1999, "Protective immunity using recombinant human IL-12 and alum as adjuvants in a primate model of cutaneous leishmaniasis," J. Immunol. 163(8):4481-8.

Kimura et al., 2000, "IL-4 production by PBMCs on stimulation with mite allergen is correlated with the level of serum IgE antibody against mite in children with bronchial asthma," J. Allergy. Clin. Immunol. 105:327-32.

Klein et al. 1997, "Demonstration of the Th1 to Th2 cytokine shift during the course of HIV-1 infection using cytoplasmic cytokine detection on single cell level by flow cytometry," AIDS 11(9):1111-8.

Leigh et al., 1998, "Th1/Th2 cytokine expression in saliva of HIV-positive and HIV-negative individuals: a pilot study in HIV-positive individuals with oropharyngeal candidiasis," J. Acquir. Immune. Defic. Syndr. Hum. Retrovirol. 19(4):373-80.

Liang et al., 1996, "Murine AIDS, a key to understanding retrovirus-induced immunodeficiency," Viral Immunol. 9(4):225-39.

Liang et al., 1997, "Prevention of immune dysfunction, vitamin E deficiency and loss of cryptosporidium resistance during murine retrovirus infection by T cell receptor peptide immunization," Nutr. Res. 17(4):677-692.

Liang et al., 1997, "Prevention of retrovirus-induced aberrant cytokine secretion, excessive lipid peroxidation, and tissue vitamin E deficiency by T cell receptor peptide treatments in C57BL/6 mice,"Proc. Soc. Exp. Biol. Med. 214(1):87-94.

Lohoff et al., 1998, "Experimental murine leishmaniasis and the Th1/Th2 cell concept," Tokai J. Exp. Clin. Med. 23(6):347-50.

Longenecker et al., 1993, "Immune responses of mice and human breast cancer patients following immunization with synthetic sialyl-Tn conjugated to KLH plus detox adjuvant," Ann. N. Y. Acad. Sci. 690:276-91.

Marchalonis et al., 1999, "Recognition of defined epitopes by affinity-purified anti-immunoglobulin fab autoantibodies isolated from HIV-infected humans," J. Mol. Recognit. 12(3):169-76.

Marchalonis et al., 1992, "Human autoantibodies reactive with synthetic autoantigens from T-cell receptor beta chain," Proc. Natl. Acad. Sci. U. S. A. 89(8):3325-9.

Marchalonis et al., 1993, "Natural human antibodies to synthetic peptide autoantigens: correlations with age and autoimmune disease," Gerontology 39(2):65-79. Abstract only.

Marchalonis et al., 1994, "Autoantibodies to T-cell receptors following infection by murine Retrovirus," Lymphology 27S:853-856.

Marchalonis et al., 1995, "Autoantibodies against peptide-defined epitopes of T-cell receptors in retrovirally infected humans and mice, " Adv. Exp. Med. Biol. 383:211-22. Abstract only.

Marchalonis et al., 1997, "Binding of himan IgG myeloma proteins to autologous T-cell receptor determinants," Crit. Rev. Immunol. 17(5-6):497-506.

Marchalonis et al., 1997, "Use of synthetic T-cell receptor derived peptides in therapy for autoimmunity and retroviral infections," The Chemist 74:3-9.

Marchalonis et al., 2000, "Epitope promiscuity of himan monoclonal autoantibodies to T-cell receptor-combining site determinants," Appl. Biochem. Biotechnol. 83(1-3):31-49.

Meroni et al., 1996, "Evidence for type 2 cytokine production and lymphocyte activation in the early phases of HIV-1 infection," AIDS 10(1):23-30.

Meziere et al., 1997, "In vivo T helper response to retro-inverso peptidomimetrics," J. Immunol. 159(7):3230-7.

Mitra et al., 1999, "Differential representations of memory T cell subsets are characteristic of polarized immunity in leprosy and atopic diseases," Int. Immunol. 11(11):1801-10.

Moraes et al., 1999, "Cytokine mRNA expression in leprosy: a possible role for interferon-gamma and interleukin-12 in reactions (RR and ENL)," Scand. J. Immunol. 50(5):541-9.

Moreland et al., 1996, "Vbeta 17 T cell receptor peptide vaccination in rheumatoid arthritis: results of phase I dose escalation study," J. Rheumatol. 23(8):1353-62.

Moreland et al., 1998, "T cell receptor peptide vaccination in rheumatoid arthritis: a placebo-controlled trial using a combination of Vbeta3, Vbeta14, and Vbeta17 peptides," Arthritis. Rheum. 41(11):1919-29.

Mosmann et al., 1986, "Two types of murine helper T cell clone. 1. Definition according to profiles of lymphokine activities and secreted proteins," J. Immunol. 136(7):2348-57.

Mosmann et al., 1991, "The role of IL-10 in crossregulation of TH1 and TH2 responses," Immunol. Today 12(3):A49-53.

Moudgil et al., 1998, "Heterogeneity of the T cell response to immunodominant determinants within hen eggwhite lysozyme of individual syngeneic hybrid F1 mice: implications for autoimmunity and infection," J. Immunol. 161(11):6046-53.

Moverare et al., 2000, "Study of the Th1/Th2 balance, including IL-10 production, in cultures of peripheral blood mononuclear cells from birch-pollen-allergic patients," Allergy 55(2):171-5.

Robey et al., 2000, "Production and characterization of monoclonal IgM autoantiboodies specific for the T-cell receptor," J. Protein Chem. 19(1):9-21. Abstract only.

Rocha et al., 1999, "Down-regulation of Th1 type of response in early human American cutaneous leishmaniasis," J. Infect. Dis. 180(5):1731-4.

Romagnani, 1995, "Biology of human TH1 and TH2 cells," J. Clin. Immunol. 15(3):121-9.

Selvey et al., 1993, "Preferential expansion and activation of V beta 5+ CD4+ T cells in murine acquired immunodeficiency syndrome," J. Immunol. 151(3):1712-22.

Sher et al., 1992, "Role of T-cell derived cytokines in the downregulations of immune responses in parasitic and retroviral infection," Immunol. Rev. 127:183-204.

Solana et al., 2000, "NK and NK/T cells in human senescence," Vaccine 18(16):1613-20.

Soudeyns et al., 1993, "The T cell receptor V beta repertoire in HIV-1 infection and disease," Semin. Imunol. 5(3):175-85.

Timm et al., 1999, "Maturation of CD4+ lymphocytes in the aged microenvironment results in a memory-enriched population," J. Immunol. 162(2):711-7.

Valentin et al., 1998, "Dual effect of interleukin 4 on HIV-1 expression: implications for viral phenotypic switch and disease progression, " Proc. Natl. Acad. Sci. U. S. A. 95(15):8886-91.

Vandenbark et al., 1996, "Treatment of multiple sclerosis with T-cell receptor peptides: results of double-blind pilot trial," Nat. Med. 2(10):1109-15.

Victor-Kobrin et al., 1989, "Structural correlates of a regulatory idiotope," Immunol. Rev. 110:151-71.

Vigano et al., 1995, "Immunologic characterization of children vertically infected with human immunodeficiency virus, with slow or rapid disease progression," J. Pediatr. 126(3):368-74.

Wang et al., 1993, "The kinetics of imbalanced cytokine production by T cells and macrophages during the murine AIDS," Adv. Biosci. 86:335-340.

Wang et al., 1994 "Anti-IL-4 monoclonal antibody and IFN-gamma administration retards development of immune dysfuction and cytokine dysregulation during murine AIDS," Immunology 83(3):384-9.

Watson et al., 1989, "Minireview: Murine models for acquires immune deficiency syndrome," Life Sciences 44:iii-xv.

Wilson et al., 1997, "Rsults of a phase I clinical trial of a T-cell receptor peptide vaccine in patients with multiple sclerosis. I. Analysis of T-cell receptor utilization in CSF cell populations," J. Neuroimmunol. 76(1-2):15-28.

Yanagi et al., 1984, "A human T cell-specific cDNA clone encodes a protein having extensive homology to immunoglobulin chains," Nature 308(5955):145-9.

Yssel et al., 2000, "Characterization of T cell subpopulations involved in the pathogenesis of asthma and allergic diseases," Int. Arch. Allergy Immunol. 121(1):10-8.

* cited by examiner

SEQUENCE LISTING

<160> NUMBER OF SEQ ID NOS: 15

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence: T-cell
      receptor-derived peptide

<400> SEQUENCE: 1

Cys Lys Pro Ile Ser Gly His Asn Ser Leu Phe Trp Tyr Arg Gln Thr
 1               5                  10                  15

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence: T-cell
      receptor-derived peptide

<400> SEQUENCE: 2

Ala Asn Tyr Gly Tyr Thr Phe Gly Ser Gly Thr Arg Leu Thr Val Val
 1               5                  10                  15

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: T-cell
      receptor-derived peptide

<400> SEQUENCE: 3

Leu Lys Ile Gln Pro Ser Glu Pro Arg Asp Ser Ala Val Tyr Leu Cys
 1               5                  10                  15

Ala

<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence: T-cell
      receptor-derived peptide

<400> SEQUENCE: 4

Leu Thr Ile Gln Arg Thr Gln Gln Glu Asp Ser Ala Val Tyr Leu Cys
 1               5                  10                  15

Ala

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: T-cell
      receptor-derived peptide

<400> SEQUENCE: 5

Leu Ile Leu Glu Ser Ala Ser Thr Asn Gln Thr Ser Met Tyr Leu Cys
 1               5                  10                  15

Ala

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: T-cell
      receptor-derived peptide

<400> SEQUENCE: 6

Leu Thr Val Ser Gly Leu Gln Ala Glu Asp Glu Ala Asp Tyr Tyr Cys
 1               5                  10                  15

Ser

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: T-cell
      receptor-derived peptide

<400> SEQUENCE: 7

Leu Ala Ile Ser Gly Leu Glu Ser Glu Asp Glu Ala Asp Tyr Tyr Cys
 1               5                  10                  15

Ala

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: T-cell
      receptor-derived peptide

```
<400> SEQUENCE: 8

Phe Thr Ile Ser Gly Leu Gln Pro Glu Asp Ile Ala Thr Tyr Tyr Cys
 1               5                  10                  15
Gln

<210> SEQ ID NO 9
<211> LENGTH: 17
<212> TYPE: PRT
<213> ORGANISM: Artificial Sequence
<220> FEATURE:
<223> OTHER INFORMATION: Description of Artificial Sequence: T-cell
      receptor-derived peptide

<400> SEQUENCE: 9

Leu Thr Ile Ser Gly Leu Glu Pro Glu Asp Phe Ala Val Tyr Tyr Cys
 1               5                  10                  15
Gln

<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: T-cell
      receptor-derived peptide

<400> SEQUENCE: 10

Leu Lys Ile Ser Arg Val Glu Ala Glu Asp Leu Gly Val Tyr Phe Cys
 1               5                  10                  15
Ser

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: T-cell
      receptor-derived peptide

<400> SEQUENCE: 11

Leu Thr Ile Asn Pro Val Glu Ala Asp Asp Val Ala Thr Tyr Tyr Cys
 1               5                  10                  15
Gln

<210> SEQ ID NO 12
<211> LENGTH: 16
<212> TYPE: PRT
<213> ORGANISM: Artificial Sequence
<220> FEATURE:
<223> OTHER INFORMATION: Description of Artificial Sequence: T-cell
      receptor-derived peptide

<400> SEQUENCE: 12

Ala Asn Tyr Gly Tyr Thr Phe Gly Ser Gly Thr Lys Leu Thr Val Val
 1               5                  10                  15

<210> SEQ ID NO 13
<211> LENGTH: 16
<212> TYPE: PRT
<213> ORGANISM: Artificial Sequence
<220> FEATURE:
<223> OTHER INFORMATION: Description of Artificial Sequence: T-cell
      receptor-derived peptide

<400> SEQUENCE: 13
```

```
Ala Asn Tyr Gly Tyr Thr Phe Gly Ser Gly Thr Glu Leu Thr Val Val
  1               5                   10                  15

<210> SEQ ID NO 14
<211> LENGTH: 16
<212> TYPE: PRT
<213> ORGANISM: Artificial Sequence
<220> FEATURE:
<223> OTHER INFORMATION: Description of Artificial Sequence: T-cell
      receptor-derived peptide

<400> SEQUENCE: 14

Ala Asn Tyr Gly Tyr Thr Phe Gly Ser Gly Thr Asp Leu Thr Val Val
  1               5                   10                  15

<210> SEQ ID NO 15
<211> LENGTH: 7
<212> TYPE: PRT
<213> ORGANISM: Artificial Sequence
<220> FEATURE:
<221> NAME/KEY: SITE
<222> LOCATION: (4)
<223> OTHER INFORMATION: Xaa=any amino acid
<220> FEATURE:
<221> NAME/KEY: SITE
<222> LOCATION: (7)
<223> OTHER INFORMATION: Xaa=Arg, Lys, Asp, Glu, His, or other charged
      amino acid molecule
<220> FEATURE:
<223> OTHER INFORMATION: Description of Artificial Sequence: T-cell
      receptor-derived peptide

<400> SEQUENCE: 15

Thr Phe Gly Xaa Gly Thr Xaa
  1               5
```

MODULATION OF IMMUNE RESPONSE AND METHODS BASED THEREON

1. FIELD OF THE INVENTION

The present invention relates to methods for the prevention and/or treatment of cardiovascular and allergic diseases and disorders, methods for inhibiting the growth of, or reducing the volume of, a solid tumor, as well as methods for preventing progression to AIDS in an HIV-positive human, by administering a peptide derived from T-cell receptors, or a derivative of the peptide. The present invention also relates to peptides derived from T-cell receptors, and derivatives of such peptides, which are useful in such methods.

2. BACKGROUND OF THE INVENTION

The immune response is a complex and dynamic process initiated by infection, autoantigens, tumor-associated antigens and transplantation that involves antigen presenting cells (macrophages or dendritic cells), antigen-specific thymus-derived lymphocytes (T-cells) that can be further discriminated into helper or cytotoxic T-cells, and antibody forming cells of the B cell lineage. The helper T cells can be further differentiated into subsets termed Th1 that produce mostly interferon-γ (IFN-γ), or interleukin-2 (IL-2), and Th2 cells that produce mainly interleukin-4 (IL-4) or interleukin-5 (IL-5). The Th1 cells function predominantly in inflammatory reactions, where they recruit macrophages and other non-lymphoid cell types in the destruction of infectious agents. The Th2-type cells help principally in the production of antibodies through interactions with B cells, and this role predisposes to the development of asthma and allergic reactivity because of the generation of the reagenic antibody IgE (Wills-Karp, 1999, Ann. Rev. Immunol. 17:255–81).

The complex interactions among the distinct cell types are regulated by the secreted cytokines, and it is now recognized that functional balance between the two subsets of T-cells is important for normal immunity (Romagnani, 1997, Immunology Today 18: 263–266; Infante-Duarte et al., 1999, Immunopathol. 21:317–338). The definition of Th1 and Th2 helper T cells is an operational one based on expression of cytokines considered characteristic of the individual subsets, although non-lymphoid cells can produce certain essential cytokines. Often, both Th1 and Th2 responses are ongoing in particular infections, especially at later stages. Th1-type responses are generally protective against intracellular parasites; whereas extra cellular parasites are better counteracted by so-called Th0 T-cells producing both Th1 and Th2 cytokines, thus generating both cellular and humoral immunity. Optimal protection against metazoan parasites such as helminths is apparently conferred by Th2 responses. Th2-type responses favor HIV progression by allowing enhanced HIV replication in CD4$^+$ T-cells, and a strong imbalance between Th1 and Th2-type cytokine production is observed in mice infected with defective leukemia virus, the so-called MAIDS model (Watson et al., 1995, J. Immunol. 155: 2282–2291; U.S. Pat. No. 5,911,990 to Marchalonis et al.).

Polarized or unbalanced allergen-specific Th2 responses are responsible for initial triggering of allergic inflammation in atopic subjects. In general, polarization of Th1/Th2 cytokine expression induced by interaction of the pathogen with the host can lead to situations destructive to the host; i.e., the Th1–Th2 shift in MAIDS. However, correction of the imbalance can restore beneficial protection to the infected animal. Th1-dependent protection and Th2-mediated susceptibility is found in the response to the intracellular parasite *Leishmania*, and in leprosy, caused by *Mycobacterium leprae*.

Thus, it would be beneficial to have compositions and methods for maintaining proper immune system functioning, i.e., proper amounts and ratios of cytokine production, in the presence of an underlying pathogenic condition. One molecule that provides for the proper functioning of the immune system and suppression of progression to AIDS in an immunodeficiency-type retrovirus-infected individual is described in U.S. Pat. No. 5,911,990 to Marchalonis et al. The molecule is a peptide that is derived from the T cell-receptor and has the amino acid sequence Cys Lys Pro Ile Ser Gly His Asn Ser Leu Phe Trp Tyr Arg Gln Thr (SEQ ID NO:1). This peptide was shown to suppress progression to AIDS and normalize aberrant Th1 and Th2 cytokine production in individuals infected with an immunodeficiency-type retrovirus.

Citation of a reference in this or in any section of the specification shall not be construed as an admission that such reference is prior art to the present invention.

3. SUMMARY OF THE INVENTION

The present invention is directed to a T-cell receptor (TCR)-derived peptide, or a derivative of the peptide, and methods for their use. The TCR-derived peptide of the present invention is selected from the group consisting of peptides comprising the amino acid sequence Cys Lys Pro Ile Ser Gly His Asn Ser Leu Phe Trp Tyr Arg Gln Thr (SEQ ID NO:1), Ala Asn Tyr Gly Tyr Thr Phe Gly Ser Gly Thr Arg Leu Thr Val Val (SEQ ID NO:2), Leu Lys Ile Gln Pro Ser Glu Pro Arg Asp Ser Ala Val Tyr Leu Cys Ala (SEQ ID NO:3), Leu Thr Ile Gln Arg Thr Gln Gln Glu Asp Ser Ala Val Tyr Leu Cys Ala (SEQ ID NO:4), Leu Ile Leu Glu Ser Ala Ser Thr Asn Gln Thr Ser Met Tyr Leu Cys Ala (SEQ ID NO:5), Leu Thr Val Ser Gly Leu Gln Ala Glu Asp Glu Ala Asp Tyr Tyr Cys Ser (SEQ ID NO:6), Leu Ala Ile Ser Gly Leu Glu Ser Glu Asp Glu Ala Asp Tyr Tyr Cys Ala (SEQ ID NO:7), Phe Thr Ile Ser Gly Leu Gln Pro Glu Asp Ile Ala Thr Tyr Tyr Cys Gln (SEQ ID NO:8), Leu Thr Ile Ser Gly Leu Glu Pro Glu Asp Phe Ala Val Tyr Tyr Cys Gln (SEQ ID NO:9), Leu Lys Ile Ser Arg Val Glu Ala Glu Asp Leu Gly Val Tyr Phe Cys Ser (SEQ ID NO:10) and Leu Thr Ile Asn Pro Val Glu Ala Asp Asp Val Ala Thr Tyr Tyr Cys Gln (SEQ ID NO:11), Ala Asn Tyr Gly Tyr Thr Phe Gly Ser Gly Thr Lys Leu Thr Val Val (SEQ ID NO:12), Ala Asn Tyr Gly Tyr Thr Phe Gly Ser Gly Thr Glu Leu Thr Val Val (SEQ ID NO:13), Ala Asn Tyr Gly Tyr Thr Phe Gly Ser Gly Thr Asp Leu Thr Val Val (SEQ ID NO:14), and Thr Phe Gly Xaa Gly Thr Yaa, wherein Xaa is any amino acid and Yaa is Arg, Lys, Asp, Glu, His or other charged amino acid molecule (SEQ ID NO:15).

The present invention is also directed to a derivative of the foregoing peptides of SEQ ID NOS:1–15. Such derivative peptides include those in which one or more amino acid residue has been replaced by a similar amino acid, residue, or the corresponding D-isomer, or by a non-naturally occurring amino acid residue. Other derivative peptides include cyclic derivatives of the peptides and chemical derivatives of the peptides of SEQ ID NOS:1–15. Other derivatives also include dual peptides or multimer peptides consisting of the same or of different peptides of SEQ ID NOS:1–15, wherein the peptides are covalently linked to one another directly or through a spacer. Other derivatives include those peptides which have insertions or deletions relative to the peptides of SEQ ID NOS:1–15.

The present invention is also directed to pharmaceutical compositions comprising a peptide of the present invention, or a derivative thereof, and a pharmaceutically acceptable carrier. The pharmaceutical compositions are used, e.g., as promoters of Th1 cytokine production and/or inhibitors of Th2 cytokine production in an individual animal, preferably a mammal, including a human.

The present invention is also directed to methods for the use of a T-cell receptor derived peptide, or a derivative thereof, to increase production of at least one Th1 cytokine and/or decrease production of at least one Th2 cytokine, comprising administering a peptide selected from the group consisting of peptides comprising the amino acid sequence Cys Lys Pro Ile Ser Gly His Asn Ser Leu Phe Trp Tyr Arg Gln Thr (SEQ ID NO:1), Ala Asn Tyr Gly Tyr Thr Phe Gly Ser Gly Thr Arg Leu Thr Val Val (SEQ ID NO:2), Leu Lys Ile Gln Pro Ser Glu Pro Arg Asp Ser Ala Val Tyr Leu Cys Ala (SEQ ID NO:3), Leu Thr Ile Gln Arg Thr Gln Gln Glu Asp Ser Ala Val Tyr Leu Cys Ala (SEQ ID NO:4), Leu Ile Leu Glu Ser Ala Ser Thr Asn Gln Thr Ser Met Tyr Leu Cys Ala (SEQ ID NO:5), Leu Thr Val Ser Gly Leu Gln Ala Glu Asp Glu Ala Asp Tyr Tyr Cys Ser (SEQ ID NO:6), Leu Ala Ile Ser Gly Leu Glu Ser Glu Asp Glu Ala Asp Tyr Tyr Cys Ala (SEQ ID NO:7), Phe Thr Ile Ser Gly Leu Gln Pro Glu Asp Ile Ala Thr Tyr Tyr Cys Gln (SEQ ID NO:8), Leu Thr Ile Ser Gly Leu Glu Pro Glu Asp Phe Ala Val Tyr Tyr Cys Gln (SEQ ID NO:9), Leu Lys Ile Ser Arg Val Glu Ala Glu Asp Leu Gly Val Tyr Phe Cys Ser (SEQ ID NO:10) and Leu Thr Ile Asn Pro Val Glu Ala Asp Asp Val Ala Thr Tyr Tyr Cys Gln (SEQ ID NO:11), Ala Asn Tyr Gly Tyr Thr Phe Gly Ser Gly Thr Lys Leu Thr Val Val (SEQ ID NO:12), Ala Asn Tyr Gly Tyr Thr Phe Gly Ser Gly Thr Glu Leu Thr Val Val (SEQ ID NO:13), Ala Asn Tyr Gly Tyr Thr Phe Gly Ser Gly Thr Asp Leu Thr Val Val (SEQ ID NO:14), and Thr Phe Gly Xaa Gly Thr Yaa, wherein Xaa is any amino acid and Yaa is Arg, Lys, Asp, Glu, His or other charged amino acid molecule (SEQ ID NO:15), or a derivative thereof, to an individual, in an amount sufficient to increase production of at least one Th1 cytokine and/or decrease production of at least one Th2 cytokine.

The present invention is also directed to methods for increasing production of at least one Th1 cytokine or decreasing production of at least one Th2 cytokine in an individual free of infection with an immunodeficiency-type retrovirus comprising administering a peptide selected from the group consisting of peptides comprising the amino acid sequence Cys Lys Pro Ile Ser Gly His Asn Ser Leu Phe Trp Tyr Arg Gln Thr (SEQ ID NO:1), Ala Asn Tyr Gly Tyr Thr Phe Gly Ser Gly Thr Arg Leu Thr Val Val (SEQ ID NO:2), Leu Lys Ile Gln Pro Ser Glu Pro Arg Asp Ser Ala Val Tyr Leu Cys Ala (SEQ ID NO:3), Leu Thr Ile Gln Arg Thr Gln Gln Glu Asp Ser Ala Val Tyr Leu Cys Ala (SEQ ID NO:4), Leu Ile Leu Glu Ser Ala Ser Thr Asn Gln Thr Ser Met Tyr Leu Cys Ala (SEQ ID NO:5), Leu Thr Val Ser Gly Leu Gln Ala Glu Asp Glu Ala Asp Tyr Tyr Cys Ser (SEQ ID NO:6), Leu Ala Ile Ser Gly Leu Glu Ser Glu Asp Glu Ala Asp Tyr Tyr Cys Ala (SEQ ID NO:7), Phe Thr Ile Ser Gly Leu Gln Pro Glu Asp Ile Ala Thr Tyr Tyr Cys Gln (SEQ ID NO:8), Leu Thr Ile Ser Gly Leu Glu Pro Glu Asp Phe Ala Val Tyr Tyr Cys Gln (SEQ ID NO:9), Leu Lys Ile Ser Arg Val Glu Ala Glu Asp Leu Gly Val Tyr Phe Cys Ser (SEQ ID NO:10) and Leu Thr Ile Asn Pro Val Glu Ala Asp Asp Val Ala Thr Tyr Tyr Cys Gln (SEQ ID NO:11), Ala Asn Tyr Gly Tyr Thr Phe Gly Ser Gly Thr Lys Leu Thr Val Val (SEQ ID NO:12), Ala Asn Tyr Gly Tyr Thr Phe Gly Ser Gly Thr Glu Leu Thr Val Val (SEQ ID NO:13), Ala Asn Tyr Gly Tyr Thr Phe Gly Ser Gly Thr Asp Leu Thr Val Val (SEQ ID NO:14), and Thr Phe Gly Xaa Gly Thr Yaa, wherein Xaa is any amino acid and Yaa is Arg, Lys, Asp, Glu, His or other charged amino acid molecule (SEQ ID NO:15), or a derivative thereof, to an individual free of infection with an immunodeficiency-type retrovirus in an amount sufficient to increase production of at least one Th1 cytokine or decrease production of at least one Th2 cytokine.

The present invention is also directed to methods for the use of a peptide or a derivative thereof for the prevention of progression to, or delay the onset of, AIDS in an immunodeficiency-type retrovirus infected individual, e.g., an HIV-infected human, comprising administering a peptide selected from the group consisting of peptides comprising the amino acid sequence Cys Lys Pro Ile Ser Gly His Asn Ser Leu Phe Trp Tyr Arg Gln Thr (SEQ ID NO:1), Ala Asn Tyr Gly Tyr Thr Phe Gly Ser Gly Thr Arg Leu Thr Val Val (SEQ ID NO:2), Leu Lys Ile Gln Pro Ser Glu Pro Arg Asp Ser Ala Val Tyr Leu Cys Ala (SEQ ID NO:3), Leu Thr Ile Gln Arg Thr Gln Gln Glu Asp Ser Ala Val Tyr Leu Cys Ala (SEQ ID NO:4), Leu Ile Leu Glu Ser Ala Ser Thr Asn Gln Thr Ser Met Tyr Leu Cys Ala (SEQ ID NO:5), Leu Thr Val Ser Gly Leu Gln Ala Glu Asp Glu Ala Asp Tyr Tyr Cys Ser (SEQ ID NO:6), Leu Ala Ile Ser Gly Leu Glu Ser Glu Asp Glu Ala Asp Tyr Tyr Cys Ala (SEQ ID NO:7), Phe Thr Ile Ser Gly Leu Gln Pro Glu Asp Ile Ala Thr Tyr Tyr Cys Gln (SEQ ID NO:8), Leu Thr Ile Ser Gly Leu Glu Pro Glu Asp Phe Ala Val Tyr Tyr Cys Gln (SEQ ID NO:9), Leu Lys Ile Ser Arg Val Glu Ala Glu Asp Leu Gly Val Tyr Phe Cys Ser (SEQ ID NO:10) and Leu Thr Ile Asn Pro Val Glu Ala Asp Asp Val Ala Thr Tyr Tyr Cys Gln (SEQ ID NO:11), Ala Asn Tyr Gly Tyr Thr Phe Gly Ser Gly Thr Lys Leu Thr Val Val (SEQ ID NO:12), Ala Asn Tyr Gly Tyr Thr Phe Gly Ser Gly Thr Glu Leu Thr Val Val (SEQ ID NO:13), Ala Asn Tyr Gly Tyr Thr Phe Gly Ser Gly Thr Asp Leu Thr Val Val (SEQ ID NO:14), and Thr Phe Gly Xaa Gly Thr Yaa, wherein Xaa is any amino acid and Yaa is Arg, Lys, Asp, Glu, His or other charged amino acid molecule (SEQ ID NO:15), or a derivative thereof, to an immunodeficiency-type retrovirus infected individual, in an amount sufficient to arrest the development of immune dysfunction or cytokine dysregulation, which allows such retrovirus infections to immunologically weaken the host, i.e., to prevent progression to, or delay the onset of, AIDS.

The present invention also provides methods for reversing the deleterious effects of infection with an immunodeficiency-type retrovirus, e.g., HIV, comprising administering a peptide selected from the group consisting of peptides comprising the amino acid sequence Cys Lys Pro Ile Ser Gly His Asn Ser Leu Phe Trp Tyr Arg Gln Thr (SEQ ID NO:1), Ala Asn Tyr Gly Tyr Thr Phe Gly Ser Gly Thr Arg Leu Thr Val Val (SEQ ID NO:2), Leu Lys Ile Gln Pro Ser Glu Pro Arg Asp Ser Ala Val Tyr Leu Cys Ala (SEQ ID NO:3), Leu Thr Ile Gln Arg Thr Gln Gln Glu Asp Ser Ala Val Tyr Leu Cys Ala (SEQ ID NO:4), Leu Ile Leu Glu Ser Ala Ser Thr Asn Gln Thr Ser Met Tyr Leu Cys Ala (SEQ ID NO:5), Leu Thr Val Ser Gly Leu Gln Ala Glu Asp Glu Ala Asp Tyr Tyr Cys Ser (SEQ ID NO:6), Leu Ala Ile Ser Gly Leu Glu Ser Glu Asp Glu Ala Asp Tyr Tyr Cys Ala (SEQ ID NO:7), Phe Thr Ile Ser Gly Leu Gln Pro Glu Asp Ile Ala Thr Tyr Tyr Cys Gln (SEQ ID NO:8), Leu Thr Ile Ser Gly Leu Glu Pro Glu Asp Phe Ala Val Tyr Tyr Cys Gln (SEQ ID NO:9), Leu Lys Ile Ser Arg Val Glu Ala Glu Asp Leu Gly Val Tyr Phe Cys Ser (SEQ ID NO:10) and Leu Thr Ile Asn Pro Val Glu Ala Asp Asp Val Ala Thr Tyr Tyr Cys Gln (SEQ ID NO:11), Ala Asn Tyr Gly Tyr Thr Phe Gly Ser Gly Thr Lys Leu Thr Val Val (SEQ ID NO:12), Ala Asn Tyr Gly Tyr Thr Phe Gly Ser Gly Thr Glu Leu Thr Val Val (SEQ ID NO:13), Ala Asn Tyr Gly Tyr Thr Phe Gly Ser Gly Thr Asp Leu Thr Val Val (SEQ ID NO:14), and Thr Phe Gly Xaa Gly Thr Yaa, wherein Xaa is any amino acid and Yaa is Arg, Lys, Asp, Glu, His or other charged amino acid molecule (SEQ ID NO:15), or a derivative thereof, to an individual infected with an immunodeficiency-type retrovirus, in an amount sufficient to reverse the deleterious effects of immunodeficiency-type retrovirus infection.

Methods of suppressing progression to immune dysfunction and cytokine dysregulation caused by HIV infection in an individual are also provided in the present invention, said method comprising administering a peptide selected from the group consisting of peptides comprising the amino acid sequence Cys Lys Pro Ile Ser Gly His Asn Ser Leu Phe Trp Tyr Arg Gln Thr (SEQ ID NO:1), Ala Asn Tyr Gly Tyr Thr Phe Gly Ser Gly Thr Arg Leu Thr Val Val (SEQ ID NO:2), Leu Lys Ile Gln Pro Ser Glu Pro Arg Asp Ser Ala Val Tyr Leu Cys Ala (SEQ ID NO:3), Leu Thr Ile Gln Arg Thr Gln Gln Glu Asp Ser Ala Val Tyr Leu Cys Ala (SEQ ID NO:4), Leu Ile Leu Glu Ser Ala Ser Thr Asn Gln Thr Ser Met Tyr Leu Cys Ala (SEQ ID NO:5), Leu Thr Val Ser Gly Leu Gln Ala Glu Asp Glu Ala Asp Tyr Tyr Cys Ser (SEQ ID NO:6), Leu Ala Ile Ser Gly Leu Gln Ser Glu Asp Glu Ala Asp Tyr Tyr Cys Ala (SEQ ID NO:7), Phe Thr Ile Ser Gly Leu Gln Pro Glu Asp Ile Ala Thr Tyr Tyr Cys Gln (SEQ ID NO:8), Leu Thr Ile Ser Gly Leu Glu Pro Glu Asp Phe Ala Val Tyr Tyr Cys Gln (SEQ ID NO:9), Leu Lys Ile Ser Arg Val Glu Ala Glu Asp Leu Gly Val Tyr Phe Cys Ser (SEQ ID NO:10) and Leu Thr Ile Asn Pro Val Glu Ala Asp Asp Val Ala Thr Tyr Tyr Cys Gln (SEQ ID NO:11), Ala Asn Tyr Gly Tyr Thr Phe Gly Ser Gly Thr Lys Leu Thr Val Val (SEQ ID NO:12), Ala Asn Tyr Gly Tyr Thr Phe Gly Ser Gly Thr Glu Leu Thr Val Val (SEQ ID NO:13), Ala Asn Tyr Gly Tyr Thr Phe Gly Ser Gly Thr Asp Leu Thr Val Val (SEQ ID NO:14), and Thr Phe Gly Xaa Gly Thr Yaa, wherein Xaa is any amino acid and Yaa is Arg, Lys, Asp, Glu, His or other charged amino acid molecule (SEQ ID NO:15), or a derivative thereof, to an individual infected with HIV in an amount sufficient to suppress or delay progression to immune dysfunction and cytokine dysregulation.

Moreover, methods for preventing immunosuppression and cytokine dysregulation induced by infection with an immunodeficiency-type retrovirus are also provided in the present invention, said method comprising administering to an individual infected with an immunodeficiency-type retrovirus a peptide selected from the group consisting of peptides comprising the amino acid sequence Cys Lys Pro Ile Ser Gly His Asn Ser Leu Phe Trp Tyr Arg Gln Thr (SEQ ID NO:1), Ala Asn Tyr Gly Tyr Thr Phe Gly Ser Gly Thr Arg Leu Thr Val Val (SEQ ID NO:2), Leu Lys Ile Gln Pro Ser Glu Pro Arg Asp Ser Ala Val Tyr Leu Cys Ala (SEQ ID NO:3), Leu Thr Ile Gln Arg Thr Gln Gin Glu Asp Ser Ala Val Tyr Leu Cys Ala (SEQ ID NO:4), Leu Ile Leu Glu Ser Ala Ser Thr Asn Gln Thr Ser Met Tyr Leu Cys Ala (SEQ ID NO:5), Leu Thr Val Ser Gly Leu Gln Ala Glu Asp Glu Ala Asp Tyr Tyr Cys Ser (SEQ ID NO:6), Leu Ala Ile Ser Gly Leu Glu Ser Glu Asp Glu Ala Asp Tyr Tyr Cys Ala (SEQ ID NO:7), Phe Thr Ile Ser Gly Leu Gln Pro Glu Asp Ile Ala Thr Tyr Tyr Cys Gln (SEQ ID NO:8), Leu Thr Ile Ser Gly Leu Glu Pro Glu Asp Phe Ala Val Tyr Tyr Cys Gln (SEQ ID NO:9), Leu Lys Ile Ser Arg Val Glu Ala Glu Asp Leu Gly Val Tyr Phe Cys Ser (SEQ ID NO:10) and Leu Thr Ile Asn Pro Val Glu Ala Asp Asp Val Ala Thr Tyr Tyr Cys Gln (SEQ ID NO:11), Ala Asn Tyr Gly Tyr Thr Phe Gly Ser Gly Thr Lys Leu Thr Val Val (SEQ ID NO:12), Ala Asn Tyr Gly Tyr Thr Phe Gly Ser Gly Thr Glu Leu Thr Val Val (SEQ ID NO:13), Ala Asn Tyr Gly Tyr Thr Phe Gly Ser Gly Thr Asp Leu Thr Val Val (SEQ ID NO:14), and Thr Phe Gly Xaa Gly Thr Yaa, wherein Xaa is any amino acid and Yaa is Arg, Lys, Asp, Glu, His or other charged amino acid molecule (SEQ ID NO:15), or a derivative thereof, in an amount sufficient to prevent immunosuppression and cytokine dysregulation induced by infection with an immunodeficiency-type retrovirus.

The present invention is also directed to methods for the prevention and/or treatment of a disease or disorder of the cardiovascular system, comprising administering a peptide selected from the group consisting of peptides comprising the amino acid sequence Cys Lys Pro Ile Ser Gly His Asn Ser Leu Phe Trp Tyr Arg Gln Thr (SEQ ID NO:1), Ala Asn Tyr Gly Tyr Thr Phe Gly Ser Gly Thr Arg Leu Thr Val Val (SEQ ID NO:2), Leu Lys Ile Gln Pro Ser Glu Pro Arg Asp Ser Ala Val Tyr Leu Cys Ala (SEQ ID NO:3), Leu Thr Ile Gln Arg Thr Gln Gin Glu Asp Ser Ala Val Tyr Leu Cys Ala (SEQ ID NO:4), Leu Ile Leu Glu Ser Ala Ser Thr Asn Gln Thr Ser Met Tyr Leu Cys Ala (SEQ ID NO:5), Leu Thr Val Ser Gly Leu Gln Ala Glu Asp Glu Ala Asp Tyr Tyr Cys Ser (SEQ ID NO:6), Leu Ala Ile Ser Gly Leu Glu Ser Glu Asp Glu Ala Asp Tyr Tyr Cys Ala (SEQ ID NO:7), Phe Thr Ile Ser Gly Leu Gln Pro Glu Asp Ile Ala Thr Tyr Tyr Cys Gln (SEQ ID NO:8), Leu Thr Ile Ser Gly Leu Glu Pro Glu Asp Phe Ala Val Tyr Tyr Cys Gln (SEQ ID NO:9), Leu Lys Ile Ser Arg Val Glu Ala Glu Asp Leu Gly Val Tyr Phe Cys Ser (SEQ ID NO:10) and Leu Thr Ile Asn Pro Val Glu Ala Asp Asp Val Ala Thr Tyr Tyr Cys Gln (SEQ ID NO:11), Ala Asn Tyr Gly Tyr Thr Phe Gly Ser Gly Thr Lys Leu Thr Val Val (SEQ ID NO:12), Ala Asn Tyr Gly Tyr Thr Phe Gly Ser Gly Thr Glu Leu Thr Val Val (SEQ ID NO:13), Ala Asn Tyr Gly Tyr Thr Phe Gly Ser Gly Thr Asp Leu Thr Val Val (SEQ ID NO:14), and Thr Phe Gly Xaa Gly Thr Yaa, wherein Xaa is any amino acid and Yaa is Arg, Lys, Asp, Glu, His or other charged amino acid molecule (SEQ ID NO:15), or a derivative thereof, to an individual in need thereof, in an amount sufficient to prevent or treat a disease or disorder of the cardiovascular system.

Illustrative disease and disorders of the cardiovascular system which can be ameliorated, prevented or treated according to the present invention include, but are not limited to, atherosclerosis, arteriosclerosis, atherosclerotic heart disease, reperfusion injury, cardiac arrest, myocardial infarction, thrombus formation, and retrovirus-induced cardiovascular dysfunction.

The present invention is also directed to methods for the prevention and/or treatment of an allergic disease or disorder characterized by increased IgE production, comprising administering a peptide selected from the group consisting of peptides comprising the amino acid sequence Cys Lys Pro Ile Ser Gly His Asn Ser Leu Phe Trp Tyr Arg Gln Thr (SEQ ID NO:1), Ala Asn Tyr Gly Tyr Thr Phe Gly Ser Gly Thr Arg Leu Thr Val Val (SEQ ID NO:2), Leu Lys Ile Gln Pro Ser Glu Pro Arg Asp Ser Ala Val Tyr Leu Cys Ala (SEQ ID NO:3), Leu Thr Ile Gln Arg Thr Gln Gln Glu Asp Ser Ala Val Tyr Leu Cys Ala (SEQ ID NO:4), Leu Ile Leu Glu Ser Ala Ser Thr Asn Gln Thr Ser Met Tyr Leu Cys Ala (SEQ ID NO:5), Leu Thr Val Ser Gly Leu Gln Ala Glu Asp Glu Ala Asp Tyr Tyr Cys Ser (SEQ ID NO:6), Leu Ala Ile Ser Gly Leu Glu Ser Glu Asp Glu Ala Asp Tyr Tyr Cys Ala (SEQ ID NO:7), Phe Thr Ile Ser Gly Leu Gin Pro Glu Asp Ile Ala Thr Tyr Tyr Cys Gln (SEQ ID NO:8), Leu Thr Ile Ser Gly Leu Glu Pro Glu Asp Phe Ala Val Tyr Tyr Cys Gln (SEQ ID NO:9), Leu Lys Ile Ser Arg Val Glu Ala Glu Asp Leu Gly Val Tyr Phe Cys Ser (SEQ ID NO:10) and Leu Thr Ile Asn Pro Val Glu Ala Asp Asp Val Ala Thr Tyr Tyr Cys Gln (SEQ ID NO:11), Ala Asn Tyr Gly Tyr Thr Phe Gly Ser Gly Thr Lys Leu Thr Val Val (SEQ ID NO:12), Ala Asn Tyr Gly Tyr Thr Phe Gly Ser Gly Thr Glu Leu Thr Val Val (SEQ ID NO:13), Ala Asn Tyr Gly Tyr Thr Phe Gly Ser Gly Thr Asp Leu Thr Val Val (SEQ ID NO:14), and Thr Phe Gly Xaa Gly Thr Yaa, wherein Xaa is any amino acid and Yaa is Arg, Lys, Asp, Glu, His or other charged amino acid molecule (SEQ ID NO:15), or a derivative thereof, to an individual in need thereof, in an amount sufficient to prevent or treat an allergic disease or disorder in which the disease or disorder is characterized by increased IgE production.

Illustrative examples of such allergic diseases and disorders characterized by increased IgE production include, but are not limited to, allergy, asthma, delayed hypersensitivity, septic shock, and anaphylactic shock.

The present invention is also directed to methods for inhibiting the growth of a solid tumor or reducing the volume of a solid tumor, comprising administering a peptide selected from the group consisting of peptide comprising the amino acid sequence Cys Lys Pro Ile Ser Gly His Asn Ser Leu Phe Trp Tyr Arg Gln Thr (SEQ ID NO:1), Ala Asn Tyr Gly Tyr Thr Phe Gly Ser Gly Thr Arg Leu Thr Val Val (SEQ ID NO:2), Leu Lys Ile Gln Pro Ser Glu Pro Arg Asp Ser Ala Val Tyr Leu Cys Ala (SEQ ID NO:3), Leu Thr Ile Gln Arg Thr Gln Gln Glu Asp Ser Ala Val Tyr Leu Cys Ala (SEQ ID NO:4), Leu Ile Leu Glu Ser Ala Ser Thr Asn Gln Thr Ser Met Tyr Leu Cys Ala (SEQ ID NO:5), Leu Thr Val Ser Gly Leu Gln Ala Glu Asp Glu Ala Asp Tyr Tyr Cys Ser (SEQ ID NO:6), Leu Ala Ile Ser Gly Leu Glu Ser Glu Asp Glu Ala Asp Tyr Tyr Cys Ala (SEQ ID NO:7), Phe Thr Ile Ser Gly Leu Gln Pro Glu Asp Ile Ala Thr Tyr Tyr Cys Gln (SEQ ID NO:8), Leu Thr Ile Ser Gly Leu Glu Pro Glu Asp Phe Ala Val Tyr Tyr Cys Gln (SEQ ID NO:9), Leu Lys Ile Ser Arg Val Glu Ala Glu Asp Leu Gly Val Tyr Phe Cys Ser (SEQ ID NO:10) and Leu Thr Ile Asn Pro Val Glu Ala Asp Asp Val Ala Thr Tyr Tyr Cys Gln (SEQ ID NO:11), Ala Asn Tyr Gly Tyr Thr Phe Gly Ser Gly Thr Lys Leu Thr Val Val (SEQ ID NO:12), Ala Asn Tyr Gly Tyr Thr Phe Gly Ser Gly Thr Glu Leu Thr Val Val (SEQ ID NO:13), Ala Asn Tyr Gly Tyr Thr Phe Gly Ser Gly Thr Asp Leu Thr Val Val (SEQ ID NO:14), and Thr Phe Gly Xaa Gly Thr Yaa, wherein Xaa is any amino acid and Yaa is Arg, Lys, Asp, Glu, His or other charged amino acid molecule (SEQ ID NO:15), or a derivative thereof, to an individual in need thereof, in an amount sufficient to inhibit the growth of, or reduce the volume of, the solid tumor.

Solid tumors include, but are not limited to sarcomas, carcinomas, lymphomas or other solid tumor cancers, such as germ line tumors and tumors of the central nervous system, including, but not limited to, breast cancer, prostate cancer, cervical cancer, uterine cancer, lung cancer, ovarian cancer, testicular cancer, thyroid cancer, astrocytoma, glioma, pancreatic cancer, stomach cancer, liver cancer, colon cancer, and melanoma.

The present invention also provides methods for preventing immunosuppression or suppressing progression to immune dysfunction or cytokine dysregulation in an individual infected with a viral, fungal or bacterial infectious agent other than an immunodeficiency-type retrovirus, comprising administering a peptide selected from the group consisting of peptides comprising the amino acid sequence Cys Lys Pro Ile Ser Gly His Asn Ser Leu Phe Trp Tyr Arg Gln Thr (SEQ ID NO:1), Ala Asn Tyr Gly Tyr Thr Phe Gly Ser Gly Thr Arg Leu Thr Val Val (SEQ ID NO:2), Leu Lys Ile Gln Pro Ser Glu Pro Arg Asp Ser Ala Val Tyr Leu Cys Ala (SEQ ID NO:3), Leu Thr Ile Gln Arg Thr Gln Gln Glu Asp Ser Ala Val Tyr Leu Cys Ala (SEQ ID NO:4), Leu Ile Leu Glu Ser Ala Ser Thr Asn Gln Thr Ser Met Tyr Leu Cys Ala (SEQ ID NO:5), Leu Thr Val Ser Gly Leu Gln Ala Glu Asp Glu Ala Asp Tyr Tyr Cys Ser (SEQ ID NO:6), Leu Ala Ile Ser Gly Leu Glu Ser Glu Asp Glu Ala Asp Tyr Tyr Cys Ala (SEQ ID NO:7), Phe Thr Ile Ser Gly Leu Gln Pro Glu Asp Ile Ala Thr Tyr Tyr Cys Gln (SEQ ID NO:8), Leu Thr Ile Ser Gly Leu Glu Pro Glu Asp Phe Ala Val Tyr Tyr Cys Gln (SEQ ID NO:9), Leu Lys Ile Ser Arg Val Glu Ala Glu Asp Leu Gly Val Tyr Phe Cys Ser (SEQ ID NO:10) and Leu Thr Ile Asn Pro Val Glu Ala Asp Asp Val Ala Thr Tyr Tyr Cys Gln (SEQ ID NO:11), Ala Asn Tyr Gly Tyr Thr Phe Gly Ser Gly Thr Lys Leu Thr Val Val (SEQ ID NO:12), Ala Asn Tyr Gly Tyr Thr Phe Gly Ser Gly Thr Glu Leu Thr Val Val (SEQ ID NO:13), Ala Asn Tyr Gly Tyr Thr Phe Gly Ser Gly Thr Asp Leu Thr Val Val (SEQ ID NO:14), and Thr Phe Gly Xaa Gly Thr Yaa, wherein Xaa is any amino acid and Yaa is Arg, Lys, Asp, Glu, His or other charged amino acid molecule (SEQ ID NO:15), or a derivative thereof, in an amount sufficient for preventing immunosuppression or suppressing progression to immune dysfunction or cytokine dysregulation in an individual infected with a viral, fungal or bacterial infectious agent other than an immunodeficiency-type retrovirus.

4. DETAILED DESCRIPTION OF THE INVENTION

4.1 Peptide and Peptide Derivatives

The peptides, peptide derivatives and pharmaceutical compositions of the present invention can increase production of at least one Th1 cytokine and/or decrease production of at least one Th2 cytokine, e.g., in an individual, in cell culture. The peptides and compositions have anti-immune activity, i.e., inhibitory effects against IgE production. The peptides and compositions also inhibit the progression to AIDS in an immunodeficiency-type retrovirus-infected individual, as well as the ability to inhibit the growth of a solid tumor or the ability to reduce the volume of a solid tumor. The peptides and compositions also can treat or prevent cardiovascular diseases or disorders. As used herein, treating or preventing a disease or disorder also encompasses ameliorating at least one symptom of such disease or disorder.

In certain embodiments, the term "purified" is used to indicate that the peptide or peptide derivative is substantially free of foreign components, such as bacterial proteins or cellular debris, with which it is normally associated as a part of its production. In a preferred embodiment, substantially free indicates that at least 75% of the foreign components have been removed. In more preferred embodiment, at least 95% of the foreign components have been removed. In other certain embodiments, "purified" indicates that the peptide or peptide derivative is 20%, 30%, 40%, 50%, 60%, 70%, 80%, 90%, 95% or 99% of the total protein of a composition.

As used herein, the term "peptide" refers to molecules having no more than 250 amino acids. In certain embodiments, the peptide has about 5 to about 200 amino acids. In other embodiments, the peptide has about 10 to about 100 amino acids. In certain preferred embodiments, the peptide has about 5 to about 25 amino acids. In yet more preferred embodiments, the peptide has about 5 to about 20 amino acids.

As used herein, the term "peptide derivative" includes cyclic peptides; peptides obtained by substitution of a natural amino acid residue by a similar amino acid, the corresponding D-stereomer, or by a non-natural amino acid residue; chemical derivatives of the peptides; dual peptides; and multimers of the peptides. The term also includes those peptide that have a deletion or insertion relative to the amino acid sequence of SEQ ID NOS:1–15. For example, a derivative of the peptides of SEQ ID NOS:3–11 is in which the 5'-most leucine residue is not present.

The term "cyclic peptides" as used herein are cyclic derivatives of the peptides of SEQ ID NOS:1–15 to which two additional amino acid residues suitable for cyclization have been added, one at the carboxyl terminus and one at the amino terminus. Thus, the cyclic peptides contain either an intramolecular disulfide bond, i.e., —S—S—, an intramolecular amide bond between the two added residues, i.e., —CONH— or —NHCO— or intramolecular S-alkyl bonds, i.e., —S—$(CH_2)_n$—CONH— or —NH—CO$(CH_2)_n$—S—, wherein n is 1 or 2. In a preferred embodiment, the peptide Cys Lys Pro Ile Ser Gly His Asn Ser Leu Phe Trp Tyr Arg Gln Thr (SEQ ID NO:1) is derivatized by the incorporation of two terminal cysteine residues and cyclized through an intramolecular S—S bond between the two incorporated cysteine residues. In yet another preferred embodiment, the peptide Ala Asn Tyr Gly Tyr Thr Phe Gly Ser Gly Thr Arg Leu Thr Val (SEQ ID NO:2) is derivatized by the incorporation of two terminal cysteine residues and cyclized through an intramolecular S—S bond between the two incorporated cysteine residues.

The cyclic derivatives containing an intramolecular disulfide bond may be prepared by conventional solid phase synthesis (Merrifield et al., 1982) while incorporating suitable S-protected cysteine or homocysteine residues at the positions selected for cyclization such as the amino and carboxyl termini (Sahm et al., 1996, J. Pharm. Pharmacol. 48(2):197). Following completion of the chain assembly, cyclization can be performed either by selective removal of the S-protecting groups with a consequent on-support oxidation of the two free corresponding SH-functions, to form S—S bonds, followed by conventional removal of the product from the support and appropriate purification procedure, or by removal of the peptide from the support along with complete side-chain deprotection, followed by oxidation of the free SH-functions in highly dilute aqueous solution.

The cyclic derivatives containing an intramolecular amide bond may be prepared by conventional solid phase synthesis while incorporating suitable amino and carboxyl side-chain protected amino acid derivatives at the positions selected for cyclization. The cyclic derivatives containing intramolecular —S-alkyl bonds can be prepared by conventional solid phase synthesis while incorporating an amino acid residue with a suitable amino-protected side chain, and a suitable S-protected cysteine or homocysteine residue at the positions selected for cyclization.

According to another embodiment, a peptide of the invention has one or more of the amino acid residues replaced by the corresponding D-amino acid residue. Thus the peptide or peptide derivative of the invention may be all-L, all-D or a D,L-peptide. In another embodiment, an amino acid residue may be replaced by a non-natural amino acid residue provided that the charge of the peptide is not substantially changed. Examples of non-naturally occurring or derivatized non-naturally occurring amino acids include Nα-methyl amino acids, Cα-methyl amino acids, β-methyl amino acids and amino acid analogs in general such as, but not being limited to, β-alanine (β-Ala), norvaline (Nva), norleucine (Nle), 4-aminobutyric acid (γ-Abu), 2-aminoisobutyric acid (Aib), 6-aminohexanoic acid (ε-Ahx), ornithine (Orn), hydroxyproline (Hyp), sarcosine, citrulline, cysteic acid, and cyclohexylalanine. In yet anther embodiment of the present invention, one or more amino acid residues can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

A chemical derivative of a peptide of SEQ ID NOS:1–15 includes, but is not limited to, a derivative containing additional chemical moieties not normally a part of the peptide provided that the derivative retains a function of the peptide. Examples of such derivatives are: (a) N-acyl derivatives of the amino terminal or of another free amino group, wherein the acyl group may be either an alkanoyl group, e.g., acetyl, hexanoyl, octanoyl; an aroyl group, e.g., benzoyl, or a blocking group such as Fmoc (fluorenylmethyl-O—CO—), carbobenzoxy (benzyl-O—CO—), monomethoxysuccinyl, naphthyl-NH—CO—, acetylaminocaproyl, adamantyl-NH—CO—; (b) esters of the carboxyl terminal or of another free carboxyl or hydroxy groups; (c) amides of the carboxyl terminal or of another free carboxyl groups produced by reaction with ammonia or with a suitable amine; (d) glycosylated derivatives; (e) phosphorylated derivatives; (f) derivatives conjugated to lipophilic moieties, e.g., caproyl, lauryl, stearoyl; and (g) derivatives conjugated to an antibody or other cellular ligands.

Also included among the chemical derivatives are those derivatives obtained by modification of the peptide bond —CO—NH—, for example, by (a) reduction to —$CH_2$—NH—; (b) alkylation to —CO—N (alkyl)—; (c) inversion to —NH—CO—.

A dual peptide according to the invention consists of two the same or different peptides of the invention covalently linked to one another or through a spacer such as by a short stretch of alanine residues or by a putative site for proteolysis by cathepsin (see U.S. Pat. No. 5,126,249 and European Patent No. 495,049 with respect to such sites). This will induce site-specific proteolysis of the preferred form into the two desired analogues. In one embodiment the dual peptide is Cys Lys Pro Ile Ser Gly His Asn Ser Leu Phe Trp Tyr Arg Gln Thr Cys Lys Pro Ile Ser Gly His Asn Ser Leu Phe Trp Tyr Arg Gln Thr (SEQ ID NO:16).

Multimers according to the invention consist of polymer molecules formed from a number of the same or different peptides or derivatives thereof. The polymerization is carried out with a suitable polymerization agent, such as 0.1% glutaraldehyde (Audibert et al., 1981, Nature 289:593).

In one aspect of the invention, the peptide derivative is more resistant to proteolytic degradation than the corresponding nonderivatized peptide. For example, a peptide derivative having D-amino acid substitution(s) in place of a L-amino acid resists proteolytic cleavage when administered to a mammal. In another aspect of the invention, the peptide derivative has increased permeability across a cell membrane than the corresponding nonderivatized peptide, e.g., those peptide derivatives having a lipophilic moiety coupled at the amino and/or carboxyl terminus. In yet another aspect, the peptide derivative has enhanced biological activity, e.g., those peptide derivatives which are dualized or multimerized peptides.

The peptides or peptide derivatives of the present invention are obtained by any method of peptide synthesis known to those of skill in the art, including synthetic and recombinant techniques. For example, the peptides or peptide derivatives can be obtained by solid phase peptide synthesis, which, in brief, consists of coupling the carboxyl group of the C-terminal amino acid to a resin and successively adding N-alpha protected amino acids. The protecting groups may be any known in the art. Before each new amino acid is added to the growing chain, the protecting group of the previous amino acid added to the chain is removed. The coupling of amino acids to appropriate resins is described by Rivier et al., U.S. Pat. No. 4,244,946. Such solid phase syntheses have been described, for example, by Merrifield, 1964, *J. Am. Chem. Soc.* 85:2149; Vale et al. 1981, *Science* 213:1394–1397; Marki et al., 1981 *J. Am. Chem. Soc.* 103:3178 and in U.S. Pat. Nos. 4,305,872 and 4,316,891. In a preferred aspect, an automated peptide synthesizer is employed.

Purification of the synthesized peptides or peptide derivatives is carried out by standard methods including chromatography (e.g., ion exchange, affinity, and sizing column chromatography), centrifugation, differential solubility, hydrophobicity, or by any other standard technique for the purification of proteins. In a preferred embodiment, thin layer chromatography is employed. In yet another preferred embodiment, high performance liquid chromatography (HPLC) under reverse phase conditions is employed to purify a peptide or peptide derivative of the present invention.

4.2 Compositions of and Methods for Use of the Peptides and Peptide Derivatives

The present invention provides methods for modulating the immune response in an individual, comprising administering a peptide selected from the group consisting of peptides comprising the amino acid sequence Cys Lys Pro Ile Ser Gly His Asn Ser Leu Phe Trp Tyr Arg Gln Thr (SEQ ID NO:1), Ala Asn Tyr Gly Tyr Thr Phe Gly Ser Gly Thr Arg Leu Thr Val Val (SEQ ID NO:2), Leu Lys Ile Gln Pro Ser Glu Pro Arg Asp Ser Ala Val Tyr Leu Cys Ala (SEQ ID NO:3), Leu Thr Ile Gln Arg Thr Gln Gln Glu Asp Ser Ala Val Tyr Leu Cys Ala (SEQ ID NO:4), Leu Ile Leu Glu Ser Ala Ser Thr Asn Gln Thr Ser Met Tyr Leu Cys Ala (SEQ ID NO:5), Leu Thr Val Ser Gly Leu Gln Ala Glu Asp Glu Ala Asp Tyr Tyr Cys Ser (SEQ ID NO:6), Leu Ala Ile Ser Gly Leu Glu Ser Glu Asp Glu Ala Asp Tyr Tyr Cys Ala (SEQ ID NO:7), Phe Thr Ile Ser Gly Leu Gln Pro Glu Asp Ile Ala Thr Tyr Tyr Cys Gln (SEQ ID NO:8), Leu Thr Ile Ser Gly Leu Glu Pro Glu Asp Phe Ala Val Tyr Tyr Cys Gln (SEQ ID NO:9), Leu Lys Ile Ser Arg Val Glu Ala Glu Asp Leu Gly Val Tyr Phe Cys Ser (SEQ ID NO:10) and Leu Thr Ile Asn Pro Val Glu Ala Asp Asp Val Ala Thr Tyr Tyr Cys Gln (SEQ ID NO:11), Ala Asn Tyr Gly Tyr Thr Phe Gly Ser Gly Thr Lys Leu Thr Val Val (SEQ ID NO:12), Ala Asn Tyr Gly Tyr Thr Phe Gly Ser Gly Thr Glu Leu Thr Val Val (SEQ ID NO:13), Ala Asn Tyr Gly Tyr Thr Phe Gly Ser Gly Thr Asp Leu Thr Val Val (SEQ ID NO:14), and Thr Phe Gly Xaa Gly Thr Yaa, wherein Xaa is any amino acid and Yaa is Arg, Lys, Asp, Glu, His or other charged amino acid molecule (SEQ ID NO:15), or a derivative thereof, to an individual in an amount sufficient to increase production of at least one Th1 cytokine, such as interleukin 2 and interferon-γ, and/or decrease production of at least one Th2 cytokine, such as interleukin-4, interleukin 5, interleukin 6, interleukin 10, and immunoglobulin G.

In one embodiment, the present invention is directed to methods for increasing production of at least one Th1 cytokine or decreasing production of at least one Th2 cytokine in an individual free of infection with an immunodeficiency-type retrovirus comprising administering an effective amount of a peptide selected from the group consisting of peptides comprising the amino acid sequence Cys Lys Pro Ile Ser Gly His Asn Ser Leu Phe Trp Tyr Arg Gln Thr (SEQ ID NO:1), Ala Asn Tyr Gly Tyr Thr Phe Gly Ser Gly Thr Arg Leu Thr Val Val (SEQ ID NO:2), Leu Lys Ile Gln Pro Ser Glu Pro Arg Asp Ser Ala Val Tyr Leu Cys Ala (SEQ ID NO:3), Leu Thr Ile Gln Arg Thr Gln Gln Glu Asp Ser Ala Val Tyr Leu Cys Ala (SEQ ID NO:4), Leu Ile Leu Glu Ser Ala Ser Thr Asn Gln Thr Ser Met Tyr Leu Cys Ala (SEQ ID NO:5), Leu Thr Val Ser Gly Leu Gln Ala Glu Asp Glu Ala Asp Tyr Tyr Cys Ser (SEQ ID NO:6), Leu Ala Ile Ser Gly Leu Glu Ser Glu Asp Glu Ala Asp Tyr Tyr Cys Ala (SEQ ID NO:7), Phe Thr Ile Ser Gly Leu Gln Pro Glu Asp Ile Ala Thr Tyr Tyr Cys Gln (SEQ ID NO:8), Leu Thr Ile Ser Gly Leu Glu Pro Glu Asp Phe Ala Val Tyr Tyr Cys Gln (SEQ ID NO:9), Leu Lys Ile Ser Arg Val Glu Ala Glu Asp Leu Gly Val Tyr Phe Cys Ser (SEQ ID NO:10) and Leu Thr Ile Asn Pro Val Glu Ala Asp Asp Val Ala Thr Tyr Tyr Cys Gln (SEQ ID NO:11), Ala Asn Tyr Gly Tyr Thr Phe Gly Ser Gly Thr Lys Leu Thr Val Val (SEQ ID NO:12), Ala Asn Tyr Gly Tyr Thr Phe Gly Ser Gly Thr Glu Leu Thr Val Val (SEQ ID NO:13), Ala Asn Tyr Gly Tyr Thr Phe Gly Ser Gly Thr Asp Leu Thr Val Val (SEQ ID NO:14), and Thr Phe Gly Xaa Gly Thr Yaa, wherein Xaa is any amino acid and Yaa is Arg, Lys, Asp, Glu, His or other charged amino acid molecule (SEQ ID NO:15), or a derivative thereof, to an individual free of infection with an immunodeficiency-type retrovirus in an amount sufficient to increase production of at least one Th1 cytokine or decrease production of at least one Th2 cytokine.

In one embodiment, the present invention provides methods for delaying progression to AIDS, comprising administering a peptide selected from the group consisting of peptides comprising the amino acid sequence Cys Lys Pro Ile Ser Gly His Asn Ser Leu Phe Trp Tyr Arg Gln Thr (SEQ ID NO:1), Ala Asn Tyr Gly Tyr Thr Phe Gly Ser Gly Thr Arg Leu Thr Val Val (SEQ ID NO:2), Leu Lys Ile Gln Pro Ser Glu Pro Arg Asp Ser Ala Val Tyr Leu Cys Ala (SEQ ID NO:3), Leu Thr Ile Gln Arg Thr Gln Gln Glu Asp Ser Ala Val Tyr Leu Cys Ala (SEQ ID NO:4), Leu Ile Leu Glu Ser Ala Ser Thr Asn Gln Thr Ser Met Tyr Leu Cys Ala (SEQ ID NO:5), Leu Thr Val Ser Gly Leu Gln Ala Glu Asp Glu Ala Asp Tyr Tyr Cys Ser (SEQ ID NO:6), Leu Ala Ile Ser Gly Leu Glu Ser Glu Asp Glu Ala Asp Tyr Tyr Cys Ala (SEQ ID NO:7), Phe Thr Ile Ser Gly Leu Gln Pro Glu Asp Ile Ala Thr Tyr Tyr Cys Gln (SEQ ID NO:8), Leu Thr Ile Ser Gly Leu Glu Pro Glu Asp Phe Ala Val Tyr Tyr Cys Gln (SEQ ID NO:9), Leu Lys Ile Ser Arg Val Glu Ala Glu Asp Leu Gly Val Tyr Phe Cys Ser (SEQ ID NO:10) and Leu Thr Ile Asn Pro Val Glu Ala Asp Asp Val Ala Thr Tyr Tyr Cys Gln (SEQ ID NO:11), Ala Asn Tyr Gly Tyr Thr Phe Gly Ser Gly Thr Lys Leu Thr Val Val (SEQ ID NO:12), Ala Asn Tyr Gly Tyr Thr Phe Gly Ser Gly Thr Glu Leu Thr Val Val (SEQ ID NO:13), Ala Asn Tyr Gly Tyr Thr Phe Gly Ser Gly Thr Asp Leu Thr Val Val (SEQ ID NO:14), and Thr Phe Gly Xaa Gly Thr Yaa, wherein Xaa is any amino acid and Yaa is Arg, Lys, Asp, Glu, His or other charged amino acid molecule (SEQ ID NO:15), or a derivative thereof, to an individual infected with an immunodeficiency-type retrovirus in an amount sufficient to delay the progression to AIDS.

The present invention also provides methods for reversing the deleterious effects of infection with an immunodeficiency-type retrovirus, comprising administering a peptide selected from the group consisting of peptides comprising the amino acid sequence Cys Lys Pro Ile Ser Gly His Asn Ser Leu Phe Trp Tyr Arg Gln Thr (SEQ ID NO:1), Ala Asn Tyr Gly Tyr Thr Phe Gly Ser Gly Thr Arg Leu Thr Val Val (SEQ ID NO:2), Leu Lys Ile Gln Pro Ser Glu Pro Arg Asp Ser Ala Val Tyr Leu Cys Ala (SEQ ID NO:3), Leu Thr Ile Gln Arg Thr Gln Gln Glu Asp Ser Ala Val Tyr Leu Cys Ala (SEQ ID NO:4), Leu Ile Leu Glu Ser Ala Ser Thr Asn Gln Thr Ser Met Tyr Leu Cys Ala (SEQ ID NO:5), Leu Thr Val Ser Gly Leu Gln Ala Glu Asp Glu Ala Asp Tyr Tyr Cys Ser (SEQ ID NO:6), Leu Ala Ile Ser Gly Leu Glu Ser Glu Asp Glu Ala Asp Tyr Tyr Cys Ala (SEQ ID NO:7), Phe Thr Ile Ser Gly Leu Gln Pro Glu Asp Ile Ala Thr Tyr Tyr Cys Gln (SEQ ID NO:8), Leu Thr Ile Ser Gly Leu Glu Pro Glu Asp Phe Ala Val Tyr Tyr Cys Gln (SEQ ID NO:9), Leu Lys Ile Ser Arg Val Glu Ala Glu Asp Leu Gly Val Tyr Phe Cys Ser (SEQ ID NO:10) and Leu Thr Ile Asn Pro Val Glu Ala Asp Asp Val Ala Thr Tyr Tyr Cys Gln (SEQ ID NO:11), Ala Asn Tyr Gly Tyr Thr Phe Gly Ser Gly Thr Lys Leu Thr Val Val (SEQ ID NO:12), Ala Asn Tyr Gly Tyr Thr Phe Gly Ser Gly Thr Glu Leu Thr Val Val (SEQ ID NO:13), Ala Asn Tyr Gly Tyr Thr Phe Gly Ser Gly Thr Asp Leu Thr Val Val (SEQ ID NO:14), and Thr Phe Gly Xaa Gly Thr Yaa, wherein Xaa is any amino acid and Yaa is Arg, Lys, Asp, Glu, His or other charged amino acid molecule (SEQ ID NO:15), or a derivative thereof, to an individual infected with an immunodeficiency-type retrovirus in an amount sufficient to reverse the deleterious effects of infection with an immunodeficiency-type retrovirus.

Methods of suppressing progression to immune dysfunction and cytokine dysregulation caused by HIV infection in an individual are also provided by the present invention, said method comprising administering a peptide selected from the group consisting of peptides comprising the amino acid sequence Cys Lys Pro Ile Ser Gly His Asn Ser Leu Phe Trp Tyr Arg Gln Thr (SEQ ID NO:1), Ala Asn Tyr Gly Tyr Thr Phe Gly Ser Gly Thr Arg Leu Thr Val Val (SEQ ID NO:2), Leu Lys Ile Gln Pro Ser Glu Pro Arg Asp Ser Ala Val Tyr Leu Cys Ala (SEQ ID NO:3), Leu Thr Ile Gln Arg Thr Gln Gln Glu Asp Ser Ala Val Tyr Leu Cys Ala (SEQ ID NO:4), Leu Ile Leu Glu Ser Ala Ser Thr Asn Gln Thr Ser Met Tyr Leu Cys Ala (SEQ ID NO:5), Leu Thr Val Ser Gly Leu Gln Ala Glu Asp Glu Ala Asp Tyr Tyr Cys Ser (SEQ ID NO:6), Leu Ala Ile Ser Gly Leu Glu Ser Glu Asp Glu Ala Asp Tyr Tyr Cys Ala (SEQ ID NO:7), Phe Thr Ile Ser Gly Leu Gln Pro Glu Asp Ile Ala Thr Tyr Tyr Cys Gln (SEQ ID NO:8), Leu Thr Ile Ser Gly Leu Glu Pro Glu Asp Phe Ala Val Tyr Tyr Cys Gln (SEQ ID NO:9), Leu Lys Ile Ser Arg Val Glu Ala Glu Asp Leu Gly Val Tyr Phe Cys Ser (SEQ ID NO:10) and Leu Thr Ile Asn Pro Val Glu Ala Asp Asp Val Ala Thr Tyr Tyr Cys Gln (SEQ ID NO:11), Ala Asn Tyr Gly Tyr Thr Phe Gly Ser Gly Thr Lys Leu Thr Val Val (SEQ ID NO:12), Ala Asn Tyr Gly Tyr Thr Phe Gly Ser Gly Thr Glu Leu Thr Val Val (SEQ ID NO:13), Ala Asn Tyr Gly Tyr Thr Phe Gly Ser Gly Thr Asp Leu Thr Val Val (SEQ ID NO:14), and Thr Phe Gly Xaa Gly Thr Yaa, wherein Xaa is any amino acid and Yaa is Arg, Lys, Asp, Glu, His or other charged amino acid molecule (SEQ ID NO:15), or a derivative thereof, in an individual infected with HIV in an amount sufficient to suppress progression to immune dysfunction and cytokine dysregulation.

Moreover, methods of preventing immunosuppression induced by infection with an immunodeficiency-type retrovirus are provided by the present invention, said method comprising administering a peptide selected from the group consisting of peptides comprising the amino acid sequence Cys Lys Pro Ile Ser Gly His Asn Ser Leu Phe Trp Tyr Arg Gln Thr (SEQ ID NO:1), Ala Asn Tyr Gly Tyr Thr Phe Gly Ser Gly Thr Arg Leu Thr Val Val (SEQ ID NO:2), Leu Lys Ile Gln Pro Ser Glu Pro Arg Asp Ser Ala Val Tyr Leu Cys Ala (SEQ ID NO:3), Leu Thr Ile Gln Arg Thr Gln Gln Glu Asp Ser Ala Val Tyr Leu Cys Ala (SEQ ID NO:4), Leu Ile Leu Glu Ser Ala Ser Thr Asn Gln Thr Ser Met Tyr Leu Cys Ala (SEQ ID NO:5), Leu Thr Val Ser Gly Leu Gln Ala Glu Asp Glu Ala Asp Tyr Tyr Cys Ser (SEQ ID NO:6), Leu Ala Ile Ser Gly Leu Glu Ser Glu Asp Glu Ala Asp Tyr Tyr Cys Ala (SEQ ID NO:7), Phe Thr Ile Ser Gly Leu Gln Pro Glu Asp Ile Ala Thr Tyr Tyr Cys Gln (SEQ ID NO:8), Leu Thr Ile Ser Gly Leu Glu Pro Glu Asp Phe Ala Val Tyr Tyr Cys Gln (SEQ ID NO:9), Leu Lys Ile Ser Arg Val Glu Ala Glu Asp Leu Gly Val Tyr Phe Cys Ser (SEQ ID NO:10) and Leu Thr Ile Asn Pro Val Glu Ala Asp Asp Val Ala Thr Tyr Tyr Cys Gln (SEQ ID NO:11), Ala Asn Tyr Gly Tyr Thr Phe Gly Ser Gly Thr Lys Leu Thr Val Val (SEQ ID NO:12), Ala Asn Tyr Gly Tyr Thr Phe Gly Ser Gly Thr Glu Leu Thr Val Val (SEQ ID NO:13), Ala Asn Tyr Gly Tyr Thr Phe Gly Ser Gly Thr Asp Leu Thr Val Val (SEQ ID NO:14), and Thr Phe Gly Xaa Gly Thr Yaa, wherein Xaa is any amino acid and Yaa is Arg, Lys, Asp, Glu, His or other charged amino acid molecule (SEQ ID NO:15), or a derivative thereof, to an individual infected with an immunodeficiency-type retrovirus in an amount sufficient to prevent immunosuppression.

In yet anther embodiment of the present invention, methods are provided for the prevention and/or treatment of a disease or disorder of the cardiovascular system, comprising administering a peptide selected from the group consisting of peptides comprising the amino acid sequence Cys Lys Pro Ile Ser Gly His Asn Ser Leu Phe Trp Tyr Arg Gln Thr (SEQ ID NO:1), Ala Asn Tyr Gly Tyr Thr Phe Gly Ser Gly Thr Arg Leu Thr Val Val (SEQ ID NO:2), Leu Lys Ile Gln Pro Ser Glu Pro Arg Asp Ser Ala Val Tyr Leu Cys Ala (SEQ ID NO:3), Leu Thr Ile Gln Arg Thr Gln Gln Glu Asp Ser Ala Val Tyr Leu Cys Ala (SEQ ID NO:4), Leu Ile Leu Glu Ser Ala Ser Thr Asn Gln Thr Ser Met Tyr Leu Cys Ala (SEQ ID NO:5), Leu Thr Val Ser Gly Leu Gln Ala Glu Asp Glu Ala Asp Tyr Tyr Cys Ser (SEQ ID NO:6), Leu Ala Ile Ser Gly Leu Glu Ser Glu Asp Glu Ala Asp Tyr Tyr Cys Ala (SEQ ID NO:7), Phe Thr Ile Ser Gly Leu Gln Pro Glu Asp Ile Ala Thr Tyr Tyr Cys Gln (SEQ ID NO:8), Leu Thr Ile Ser Gly Leu Glu Pro Glu Asp Phe Ala Val Tyr Tyr Cys Gln (SEQ ID NO:9), Leu Lys Ile Ser Arg Val Glu Ala Glu Asp Leu Gly Val Tyr Phe Cys Ser (SEQ ID NO:10) and Leu Thr Ile Asn Pro Val Glu Ala Asp Asp Val Ala Thr Tyr Tyr Cys Gln (SEQ ID NO:11), Ala Asn Tyr Gly Tyr Thr Phe Gly Ser Gly Thr Lys Leu Thr Val Val (SEQ ID NO:12), Ala Asn Tyr Gly Tyr Thr Phe Gly Ser Gly Thr Glu Leu Thr Val Val (SEQ ID NO:13), Ala Asn Tyr Gly Tyr Thr Phe Gly Ser Gly Thr Asp Leu Thr Val Val (SEQ ID NO:14), and Thr Phe Gly Xaa Gly Thr Yaa, wherein Xaa is any amino acid and Yaa is Arg, Lys, Asp, Glu, His or other charged amino acid molecule (SEQ ID NO:15), or a derivative thereof, to an individual in need thereof, in an amount sufficient to prevent or treat a disease or disorder of the cardiovascular system. Illustrative disease and disorders of the cardiovascular system which can be ameliorated, prevented or treated according to the present invention include, but are not limited to, atherosclerosis, arteriosclerosis, atherosclerotic heart disease, reperfusion injury, cardiac arrest, myocardial infarction, thrombus formation, and retrovirus-induced cardiovascular dysfunction.

In yet another embodiment, the present invention is directed to methods for the prevention and/or treatment of an allergic disease or disorder characterized by increased IgE production, comprising administering a peptide selected from the group consisting of peptides comprising the amino acid sequence Cys Lys Pro Ile Ser Gly His Asn Ser Leu Phe Trp Tyr Arg Gln Thr (SEQ ID NO:1), Ala Asn Tyr Gly Tyr Thr Phe Gly Ser Gly Thr Arg Leu Thr Val Val (SEQ ID NO:2), Leu Lys Ile Gln Pro Ser Glu Pro Arg Asp Ser Ala Val Tyr Leu Cys Ala (SEQ ID NO:3), Leu Thr Ile Gln Arg Thr Gln Gln Glu Asp Ser Ala Val Tyr Leu Cys Ala (SEQ ID NO:4), Leu Ile Leu Glu Ser Ala Ser Thr Asn Gln Thr Ser Met Tyr Leu Cys Ala (SEQ ID NO:5), Leu Thr Val Ser Gly Leu Gln Ala Glu Asp Glu Ala Asp Tyr Tyr Cys Ser (SEQ ID NO:6), Leu Ala Ile Ser Gly Leu Glu Ser Glu Asp Glu Ala Asp Tyr Tyr Cys Ala (SEQ ID NO:7), Phe Thr Ile Ser Gly Leu Gln Pro Glu Asp Ile Ala Thr Tyr Tyr Cys Gln (SEQ ID NO:8), Leu Thr Ile Ser Gly Leu Glu Pro Glu Asp Phe Ala Val Tyr Tyr Cys Gln (SEQ ID NO:9), Leu Lys Ile Ser Arg Val Glu Ala Glu Asp Leu Gly Val Tyr Phe Cys Ser (SEQ ID NO:10) and Leu Thr Ile Asn Pro Val Glu Ala Asp Asp Val Ala Thr Tyr Tyr Cys Gln (SEQ ID NO:11), Ala Asn Tyr Gly Tyr Thr Phe Gly Ser Gly Thr Lys Leu Thr Val Val (SEQ ID NO:12), Ala Asn Tyr Gly Tyr Thr Phe Gly Ser Gly Thr Glu Leu Thr Val Val (SEQ ID NO:13), Ala Asn Tyr Gly Tyr Thr Phe Gly Ser Gly Thr Asp Leu Thr Val Val (SEQ ID NO:14), and Thr Phe Gly Xaa Gly Thr Yaa, wherein Xaa is any amino acid and Yaa is Arg, Lys, Asp, Glu, His or other charged amino acid molecule (SEQ ID NO:15), or a derivative thereof, to an individual in need thereof, in an amount sufficient to prevent or treat an allergic disease or disorder, in which the disease or disorder is characterized by increased IgE production. Illustrative examples of such allergic diseases and disorders characterized by increased IgE production include, but are not limited to, allergy, asthma, delayed hypersensitivity, septic shock, and anaphylactic shock.

In yet another embodiment, the present invention is also directed to methods for inhibiting the growth of a solid tumor or reducing the volume of a solid tumor, comprising administering a peptide selected from the group consisting of peptides comprising the amino acid sequence Cys Lys Pro Ile Ser Gly His Asn Ser Leu Phe Trp Tyr Arg Gln Thr (SEQ ID NO:1), Ala Asn Tyr Gly Tyr Thr Phe Gly Ser Gly Thr Arg Leu Thr Val Val (SEQ ID NO:2), Leu Lys Ile Gln Pro Ser Glu Pro Arg Asp Ser Ala Val Tyr Leu Cys Ala (SEQ ID NO:3), Leu Thr Ile Gln Arg Thr Gln Gln Glu Asp Ser Ala Val Tyr Leu Cys Ala (SEQ ID NO:4), Leu Ile Leu Glu Ser Ala Ser Thr Asn Gln Thr Ser Met Tyr Leu Cys Ala (SEQ ID NO:5), Leu Thr Val Ser Gly Leu Gln Ala Glu Asp Glu Ala Asp Tyr Tyr Cys Ser (SEQ ID NO:6), Leu Ala Ile Ser Gly Leu Glu Ser Glu Asp Glu Ala Asp Tyr Tyr Cys Ala (SEQ ID NO:7), Phe Thr Ile Ser Gly Leu Gln Pro Glu Asp Ile Ala Thr Tyr Tyr Cys Gln (SEQ ID NO:8), Leu Thr Ile Ser Gly Leu Glu Pro Glu Asp Phe Ala Val Tyr Tyr Cys Gln (SEQ ID NO:9), Leu Lys Ile Ser Arg Val Glu Ala Glu Asp Leu Gly Val Tyr Phe Cys Ser (SEQ ID NO:10) and Leu Thr Ile Asn Pro Val Glu Ala Asp Asp Val Ala Thr Tyr Tyr Cys Gln (SEQ ID NO:11), Ala Asn Tyr Gly Tyr Thr Phe Gly Ser Gly Thr Lys Leu Thr Val Val (SEQ ID NO:12), Ala Asn Tyr Gly Tyr Thr Phe Gly Ser Gly Thr Glu Leu Thr Val Val (SEQ ID NO:13), Ala Asn Tyr Gly Tyr Thr Phe Gly Ser Gly Thr Asp Leu Thr Val Val (SEQ ID NO:14), and Thr Phe Gly Xaa Gly Thr Yaa, wherein Xaa is any amino acid and Yaa is Arg, Lys, Asp, Glu, His or other charged amino acid molecule (SEQ ID NO:15), or a derivative thereof, to an individual having a solid tumor, in an amount sufficient to inhibit the growth of, or reduce the volume of, the solid tumor. Solid tumors include, but are not limited to sarcomas, carcinomas, lymphomas or other solid tumor cancers, such as germ line tumors and tumors of the central nervous system, including, but not limited to, breast cancer, prostate cancer, cervical cancer, uterine cancer, lung cancer, ovarian cancer, testicular cancer, thyroid cancer, astrocytoma, glioma, pancreatic cancer, stomach cancer, liver cancer, colon cancer, and melanoma.

The present invention also provides methods for preventing immunosuppression or suppressing progression to immune dysfunction or cytokine dysregulation in an individual infected with a viral, fungal or bacterial infectious agent other than an immunodeficiency-type retrovirus, comprising administering a peptide selected from the group consisting of peptides comprising the amino acid sequence Cys Lys Pro Ile Ser Gly His Asn Ser Leu Phe Trp Tyr Arg Gln Thr (SEQ ID NO:1), Ala Asn Tyr Gly Tyr Thr Phe Gly Ser Gly Thr Arg Leu Thr Val Val (SEQ ID NO:2), Leu Lys Ile Gln Pro Ser Glu Pro Arg Asp Ser Ala Val Tyr Leu Cys Ala (SEQ ID NO:3), Leu Thr Ile Gln Arg Thr Gln Gln Glu Asp Ser Ala Val Tyr Leu Cys Ala (SEQ ID NO:4), Leu Ile Leu Glu Ser Ala Ser Thr Asn Gln Thr Ser Met Tyr Leu Cys Ala (SEQ ID NO:5), Leu Thr Val Ser Gly Leu Gln Ala Glu Asp Glu Ala Asp Tyr Tyr Cys Ser (SEQ ID NO:6), Leu Ala Ile Ser Gly Leu Glu Ser Glu Asp Glu Ala Asp Tyr Tyr Cys Ala (SEQ ID NO:7), Phe Thr Ile Ser Gly Leu Gln Pro Glu Asp Ile Ala Thr Tyr Tyr Cys Gln (SEQ ID NO:8), Leu Thr Ile Ser Gly Leu Glu Pro Glu Asp Phe Ala Val Tyr Tyr Cys Gln (SEQ ID NO:9), Leu Lys Ile Ser Arg Val Glu Ala Glu Asp Leu Gly Val Tyr Phe Cys Ser (SEQ ID NO:10) and Leu Thr Ile Asn Pro Val Glu Ala Asp Asp Val Ala Thr Tyr Tyr Cys Gln (SEQ ID NO:11), Ala Asn Tyr Gly Tyr Thr Phe Gly Ser Gly Thr Lys Leu Thr Val Val (SEQ ID NO:12), Ala Asn Tyr Gly Tyr Thr Phe Gly Ser Gly Thr Glu Leu Thr Val Val (SEQ ID NO:13), Ala Asn Tyr Gly Tyr Thr Phe Gly Ser Gly Thr Asp Leu Thr Val Val (SEQ ID NO:14), and Thr Phe Gly Xaa Gly Thr Yaa, wherein Xaa is any amino acid and Yaa is Arg, Lys, Asp, Glu, His or other charged amino acid molecule (SEQ ID NO:15), or a derivative thereof, in an amount sufficient for preventing immunosuppression or suppressing progression to immune dysfunction or cytokine dysregulation in an individual infected with a viral, fungal or bacterial infectious agent other than an immunodeficiency-type retrovirus.

The individual administered a peptide or peptide derivative of the present invention is an animal, including but not limited to animals such as cows, sheep, pigs, chickens, etc., preferably a mammal, and most preferably a human. Moreover, the individual may or may not be infected with an infectious agent, e.g., viral, fungal, bacterial, which infection results in immune dysfunction or cytokine dysregulation, e.g., infection with an immunodeficiency-type retrovirus.

Various delivery systems are known and can be used to administer a peptide or peptide derivative or a composition comprising a peptide or peptide derivative of the present invention ("Therapeutic"), e.g., encapsulation in liposomes, microparticles, microcapsules, expression by recombinant cells, receptor-mediated endocytosis (see, e.g., Wu and Wu, 1987, J. Biol. Chem. 262:4429–4432), construction of a Therapeutic-encoding nucleic acid as part of a retroviral or other vector, etc. Methods of introduction include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention systemically, e.g., via the blood stream. In yet another specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of a malignant solid tumor.

In another embodiment, the Therapeutic can be delivered in a vesicle, in particular a liposome (see Langer, Science 249:1527–1533 (1990); Treat et al., in Liposomes in the Therapy of Infectious Disease and Cancer, Lopez-Berestein and Fidler (eds.), Liss, New York, pp. 353–365 (1989); Lopez-Berestein, ibid., pp. 317–327; see generally ibid.)

In yet another embodiment, the Therapeutic can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115–138 (1984)).

Other controlled release systems are discussed in the review by Langer (Science 249:1527–1533 (1990)).

In a specific embodiment where the Therapeutic is a nucleic acid encoding a peptide or peptide derivative of the present invention, the nucleic acid can be administered in vivo to promote expression of its encoded peptide or derivative, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeoboxlike peptide which is known to enter the nucleus (see e.g., Joliot et al., 1991, Proc. Natl. Acad. Sci. USA 88:1864–1868), etc. Alternatively, a nucleic acid Therapeutic can be introduced intracellularly and incorporated within host cell DNA for expression, by homologous recombination.

The present invention also provides pharmaceutical compositions. Such compositions comprise a therapeutically effective amount of a peptide or peptide derivative of the present invention ("Therapeutic"), and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the Therapeutic, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The Therapeutics can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The compositions can also contain an adjuvant such as alum, Freund's complete or incomplete adjuvants, poly (AU) or RIBI adjuvant, or coupled to a carrier such as albumin, ovalbumin, or other native or engineered protein.

The present invention also provides for the modification of the peptide or peptide derivative such that it is more stable once administered to an individual, i.e., once administered it has a longer time period of effectiveness as compared to unmodified peptide. Such modifications are well know to those of skill in the art, e.g., polyethylene glycol derivatization (PEGylation), microencapsulation, etc.

The amount of the Therapeutic of the invention which will be effective in the treatment of a particular disorder or condition will depend on the nature of the disorder or condition, and can be determined by standard clinical techniques. In addition, in vitro assays may optionally be employed to help identify optimal dosage ranges, e.g., assays measuring the effect of a Therapeutic on Th1 or Th2 cytokine production in cell culture. The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 1–1000 micrograms of active compound per kilogram body weight, more preferably about 5–500 mg/kg body weight. Effective doses may be extrapolated from dose-response curves derived from in vitro or animal model test systems. Moreover, the compositions can be administered in multiple doses over a period of time.

In one illustrative embodiment, doses of 5 mg/kg of body weight to 25 mg/kg of body weight of the peptide comprising the sequence Cys Lys Pro Ile Ser Gly His Asn Ser Leu Phe Trp Tyr Arg Gln Thr (SEQ ID NO:1) in saline are administered in divided doses following infection with an immunodeficiency-type retrovirus. Preferably, doses of approximately 10 mg/kg of body weight to 25 mg/kg of body weight of the peptide of SEQ ID NO:1 in saline are administered in divided doses. Most preferably, doses of 10 mg/kg of body weight are administered. Multiple doses administered approximately once per month increase the efficacy of the peptide therapy. Dosage amounts, however, may vary depending on the route of administration and depending on whether the peptide is administered with or without adjuvant.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

Various publications are cited herein, the disclosures of which are incorporated by reference herein in their entirety.

What is claimed is:

1. A method to increase production of at least one Th1 cytokine or to decrease production of at least one Th2 cytokine, comprising administering to a human an effective amount of a peptide to increase production of at least one Th1 cytokine or to decrease production of at least one Th2 cytokine, said peptide consisting of the amino acid sequence Cys Lys Pro Ile Ser Gly His Asn Ser Leu Phe Trp Tyr Arg Gln Thr (SEQ ID NO:1), and which human is free of infection with an immunodeficiency-type retrovirus.

2. The method according to claim 1 in which the Th1 cytokine is selected from the group consisting of interleukin 2 and interferon-γ.

3. The method according to claim 1 in which the Th2 cytokine is selected from the group consisting of interleukin-4, interleukin 5, interleukin 6, and interleukin 10.

4. A method to increase production of at least one Th1 cytokine or to decrease production of immunoglobulin G, comprising administering to a human an effective amount of a peptide to increase production of at least one Th1 cytokine or to decrease production of immunoglobulin G, said peptide consisting of the amino acid sequence Cys Lys Pro Ile Ser Gly His Asn Ser Leu Phe Trp Tyr Arg Gln Thr (SEQ ID NO:1), and which human is free of infection with an immunodeficiency-type retrovirus.

* * * * *